United States Patent
Anantharamaiah et al.

(10) Patent No.: US 11,707,914 B2
(45) Date of Patent: *Jul. 25, 2023

(54) MEDICAL PROTECTIVE CLOTHING MATERIALS

(71) Applicant: Hollingsworth & Vose Company, East Walpole, MA (US)

(72) Inventors: Nagendra Anantharamaiah, Mysore (IN); Mark A. Gallimore, Floyd, VA (US)

(73) Assignee: Hollingsworth & Vose Company, East Walpole, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/442,723

(22) Filed: Jun. 17, 2019

(65) Prior Publication Data

US 2020/0070472 A1 Mar. 5, 2020

Related U.S. Application Data

(63) Continuation of application No. 15/661,108, filed on Jul. 27, 2017, now Pat. No. 10,322,562.

(51) Int. Cl.
*A41D 31/102* (2019.01)
*A61B 46/00* (2016.01)
(Continued)

(52) U.S. Cl.
CPC ............... *B32B 5/26* (2013.01); *A41D 13/12* (2013.01); *A41D 13/1209* (2013.01);
(Continued)

(58) Field of Classification Search
CPC ............. A41D 13/12; A41D 2400/20; A41D 2500/30; A41D 2500/50; A41D 31/0016;
(Continued)

(56) References Cited

U.S. PATENT DOCUMENTS 5,308,691 A 5/1994 Lim et al.
5,498,463 A 3/1996 McDowall et al.
(Continued)

FOREIGN PATENT DOCUMENTS

CN 102115954 A 7/2011
DE 20121010313 A1 11/2013
(Continued)

OTHER PUBLICATIONS

PCT/US18/43841, Oct. 11, 2018, International Search Report and Written Opinion.
(Continued)

*Primary Examiner* — Arti Singh-Pandey
(74) *Attorney, Agent, or Firm* — Wolf, Greenfield & Sacks, P.C.

(57) ABSTRACT

Protective clothing materials and related methods and garments are provided. In some embodiments, a protective clothing material may comprise a fibrous layer that serves as a barrier to certain fluids (e.g., bodily fluids, water) and microbes. The impermeability of the fibrous layer may be due, at least in part, to the structural uniformity and/or relatively small pore size of the fibrous layer. In some embodiments, the fibrous layer may have a relatively high air permeability that imparts beneficial properties (e.g., relatively high air flow, breathability) to the protective clothing material without adversely affecting its protection rating. In certain embodiments, the protective clothing material may also comprise one or more coarse nonwoven webs that impart beneficial properties (e.g., splash resistance) to the protective clothing material. The protective clothing materials, described herein, may be particularly useful for a wide variety of applications, including the formation of AAMI level 4 protective garments.

11 Claims, 5 Drawing Sheets

(51) Int. Cl.
| | |
|---|---|
| *D04H 1/559* | (2012.01) |
| *A41D 13/12* | (2006.01) |
| *D04H 1/4374* | (2012.01) |
| *A41H 43/04* | (2006.01) |
| *D04H 1/56* | (2006.01) |
| *B32B 5/26* | (2006.01) |
| *B32B 5/02* | (2006.01) |
| *B32B 7/02* | (2019.01) |
| *B32B 7/12* | (2006.01) |
| *B32B 37/12* | (2006.01) |
| *B32B 37/14* | (2006.01) |
| *B32B 37/18* | (2006.01) |
| *B32B 38/00* | (2006.01) |

(52) U.S. Cl.
CPC ........... *A41D 31/102* (2019.02); *A41H 43/04* (2013.01); *A61B 46/00* (2016.02); *A61B 46/40* (2016.02); *B32B 5/022* (2013.01); *B32B 7/02* (2013.01); *B32B 7/12* (2013.01); *B32B 37/12* (2013.01); *B32B 37/144* (2013.01); *B32B 37/185* (2013.01); *B32B 38/0012* (2013.01); *D04H 1/4374* (2013.01); *D04H 1/559* (2013.01); *D04H 1/56* (2013.01); *A41D 2500/30* (2013.01); *A41D 2500/50* (2013.01); *B32B 2038/0064* (2013.01); *B32B 2262/0253* (2013.01); *B32B 2305/28* (2013.01); *B32B 2307/724* (2013.01); *B32B 2323/10* (2013.01); *B32B 2535/00* (2013.01); *B32B 2571/00* (2013.01)

(58) Field of Classification Search
CPC .................... A41H 43/04; A61B 46/40; B32B 2038/0064; B32B 2262/0253; B32B 2305/28; B32B 2307/724; B32B 2323/10; B32B 2535/00; B32B 37/12; B32B 37/144; B32B 37/185; B32B 38/0012; B32B 5/022; B32B 5/26; B32B 7/02; D04H 1/56
See application file for complete search history.

(56) References Cited

U.S. PATENT DOCUMENTS

| | | |
|---|---|---|
| 5,580,459 A | 12/1996 | Powers et al. |
| 5,672,399 A | 9/1997 | Kahlbaugh et al. |
| 5,730,923 A | 3/1998 | Hassenboehler, Jr. et al. |
| 5,785,725 A | 7/1998 | Cusick et al. |
| 6,171,684 B1 | 1/2001 | Kahlbaugh et al. |
| 6,176,952 B1 | 1/2001 | Maugans et al. |
| 6,413,344 B2 | 7/2002 | Bodaghi |
| 7,008,465 B2 | 3/2006 | Graham et al. |
| 7,070,884 B2 | 7/2006 | Thompson et al. |
| 7,137,510 B1 | 11/2006 | Klein et al. |
| 7,314,497 B2 | 1/2008 | Kahlbaugh et al. |
| 7,441,667 B2 | 10/2008 | Galvin et al. |
| 7,452,832 B2 | 11/2008 | Bansal et al. |
| 10,322,562 B2 * | 6/2019 | Anantharamaiah .......................... B32B 38/0012 |
| 2006/0134388 A1 | 6/2006 | Miller et al. |
| 2009/0120048 A1 | 5/2009 | Wertz et al. |
| 2010/0263108 A1 | 10/2010 | Marin et al. |
| 2010/0320138 A1 * | 12/2010 | Waller, Jr. .............. B01D 63/14 210/338 |
| 2012/0152824 A1 | 6/2012 | Cox et al. |
| 2012/0318754 A1 | 12/2012 | Cox et al. |
| 2014/0284267 A1 * | 9/2014 | Jung .................. B01D 67/0016 210/483 |
| 2014/0308867 A1 * | 10/2014 | Van Emmerick ........ D06B 1/04 442/189 |
| 2016/0113340 A1 | 4/2016 | Levit et al. |
| 2017/0246832 A1 | 8/2017 | Moody, III et al. |

FOREIGN PATENT DOCUMENTS

| | | |
|---|---|---|
| GB | 2 496 244 A | 5/2013 |
| JP | H11-050375 A | 2/1999 |

OTHER PUBLICATIONS

International Search Report and Written Opinion for PCT/US18/43841 dated Oct. 11, 2018.

[No Author Listed], ASTM International "F316-03 (2011) Standard Test Methods for Pore Size Characteristics of Membrane Filters by Bubble Point and Mean Flow Pore Test" (2011):7 pages.

Yan et al., Prediction of Hydrostatic Pressure and Blood Penetration of Medical Protective Clothing. Journal of Engineered Fibers and Fabrics. 2016;11(1):17-22.

* cited by examiner

MEDICAL PROTECTIVE CLOTHING MATERIALS

RELATED APPLICATIONS

This application is a continuation of U.S. application Ser. No. 15/661,108 (now U.S. Pat. No. 10,322,562), filed Jul. 27, 2017, which is incorporated herein by reference in its entirety.

FIELD OF INVENTION

The present embodiments relate generally to protective clothing materials, and specifically, to protective clothing materials that prevent and/or are impermeable to penetration by certain fluids and microbes.

BACKGROUND

Healthcare workers are at risk of exposure to pathogenic microbes via contact with bodily fluids (e.g., blood, urine, saliva, sweat, feces, vomit, breast milk, semen) or other carriers (e.g., lint, sloughed skin). The use of protective clothing (e.g., surgical gowns, surgical hoods, isolation gowns, and coveralls) that act as a barrier to bodily fluids and other carriers eliminate or reduce exposure, and therefore prevent the transfer of pathogenic microbes between, e.g., patients and healthcare workers. However, the use of defective or inappropriate protective clothing may result in the unintended penetration of a carrier through the clothing (e.g., strikethrough) and the subsequent ability for microbes present in the carrier to directly contact the wearer. Depending on the application, protective clothing may be designed to offer different levels of protection from carriers and microbes.

SUMMARY OF INVENTION

Protective clothing materials that prevent and/or are impermeable to penetration by certain fluids and microbes, and related components, systems, and methods associated therewith are provided. The subject matter of this application involves, in some cases, interrelated products, alternative solutions to a particular problem, and/or a plurality of different uses of structures and compositions.

In some aspects, a protective clothing material is provided. The material comprises a fibrous layer comprising synthetic fibers. A mean flow pore size of the fibrous layer is greater than or equal to about 1 micron and less than or equal to about 6 microns. A maximum pore size of the fibrous layer is greater than or equal to about 4 micron and less than or equal to about 12 microns. A difference between the maximum pore size and the mean pore size is less than or equal to about 6 microns. An air permeability of the fibrous layer is greater than or equal to about 4 CFM and less than or equal to about 10 CFM.

In some aspects, a protective clothing material is provided. The material comprises a fibrous layer comprising synthetic fiber. A mean flow pore size of the fibrous layer is greater than or equal to about 1 micron and less than or equal to about 6 microns. A standard deviation of the mean flow pore size of the fibrous layer is greater than or equal to about 0 microns and less than or equal to about 1 micron. A standard deviation of an air permeability of the fibrous layer is greater than or equal to about 0 CFM and less than or equal to about 1 CFM.

In some aspects, a protective clothing material is provided. The material comprises a first coarse fiber layer and a second coarse fiber layer. The material further comprises a fibrous layer positioned between the first and the second coarse fiber layers. The fibrous layer comprises a meltblown fiber web, has a mean flow pore size of greater than or equal to about 1 micron and less than or equal to about 6 microns, has an air permeability of greater than or equal to about 1 CFM and less than or equal to about 10 CFM, and has a basis weight of greater than or equal to about 10 g/m² and less than or equal to about 50 g/m².

In some aspects, a method of forming a protective clothing material is provided. The method comprises providing a plurality of nonwoven webs and calendering the plurality of nonwoven webs to form a fibrous layer. The fibrous layer has an air permeability of greater than or equal to about 4 CFM and less than or equal to about 10 CFM, an air permeability uniformity of the layer is greater than or equal to about 0 and less than or equal to about 1, and a mean flow pore size of greater than or equal to about 1 micron and less than or equal to about 6 microns. The method further comprises adhering a coarse fiber layer to at least one surface of the fibrous layer using an adhesive.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
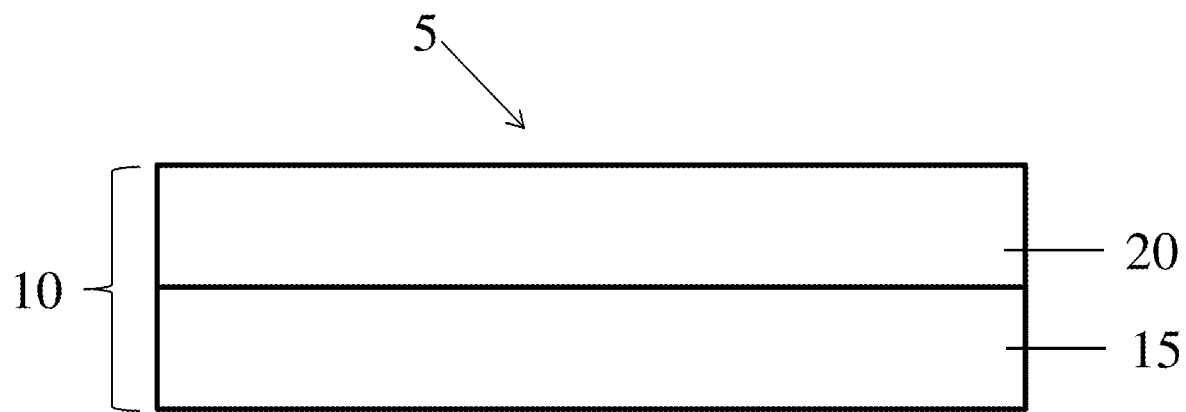
FIG. 1 is a schematic of a protective clothing material according to certain embodiments.

Protective clothing materials and related methods and garments are provided. In some embodiments, a protective clothing material may comprise a fibrous layer that serves as a barrier (e.g., impermeable barrier) to certain fluids (e.g., bodily fluids, water) and microbes (e.g., bacteria, fungi, viruses). The barrier properties of the fibrous layer may be due, at least in part, to the structural uniformity (e.g., pore size uniformity, air permeability uniformity), suitable basis weight, and/or relatively small pore size (e.g., mean flow pore size, maximum pore size) of the fibrous layer. In some embodiments, the fibrous layer may have a relatively high air permeability that imparts beneficial properties (e.g., relatively high air flow, breathability) to the protective clothing material without adversely affecting its protection rating (e.g., ANSI/AAMI level 4). In certain embodiments, the protective clothing material may also comprise one or more coarse fiber layers (e.g., spunbond web) that imparts beneficial properties (e.g., splash resistance) to the protective clothing material. The protective clothing materials, described herein, may be particularly useful for a wide variety of applications, including the formation of ANSI/AAMI level 4 protective garments (e.g., surgical apparel, surgical drapes, surgical gowns, surgical hoods).

Many clinical environments require healthcare workers to wear protective clothing that meet certain protection level standards. For example, during surgical operations, healthcare workers need to wear the American National Standards Institute (i.e., ANSI)/Association for the Advancement of Medical Instrumentation (i.e., AAMI) level 4 (i.e., highest protection level) protective clothing. In some existing protective clothing, a tradeoff exists between protection rating (e.g., level 4) and features important to wearability (e.g., comfort), such as light weight, breathability, and good air permeability. For instance, some existing protective clothing utilizes a thin polymer film to form lightweight level 4 protective clothing. However, the thin polymer film can significantly reduce air permeability and/or breathability (e.g., moisture vapor transmission rate). During long surgical operations (e.g., 2-12 hours), the low exchange of heat and/or sweat as a result of low air permeability and/or breathability can adversely affect a surgeon's performance. Accordingly, there is a need for protective clothing that can achieve the requisite protection rating for a given application without sacrificing wearablity.

In some embodiments, a fibrous layer having a relatively low pore size (e.g., mean flow pore size, maximum pore size), suitable basis weight, and/or high structural uniformity can be used to produce protective clothing material having the requisite protection rating and good wearability (e.g., comfort). Protective clothing comprising such a fibrous layer as described herein, does not suffer from one or more limitations of existing protective clothing. Without being bound by theory, it is believed that the relatively small pore size serves to reduce or eliminate the transmission of fluids (e.g., bodily fluids) and microbes. A fibrous layer having a relatively large pore size may allow for the penetration of bodily fluids and microbes (e.g., strikethrough). It is also believed that the structural uniformity (e.g., in pore size, in air permeability) allows the fibrous layer to have relatively uniform resistance to transmission throughout the layer, and accordingly the protective clothing material. Structural non-uniformity, such as a relatively large variance in pore size or air permeability, may result in non-uniformity in the resistance to transmission throughout the layer and ultimately allow bodily fluids and/or microbes to penetrate at areas of low resistance. It is also believed that the suitable basis weights, described herein, allow the fibrous layer to have a sufficient fiber density to form a tortuous path that traps fluids and/or microbes while maintaining features important to wearability (e.g., light weight, breathability).

In some embodiments, a protective clothing material may comprise a fibrous layer having a relatively small pore size (e.g., mean flow pore size, maximum pore size), a suitable basis weight, and/or high structural uniformity. The fibrous layer may include one or more nonwoven webs (e.g., meltblown fiber webs). In some embodiments, two or more nonwoven webs (e.g., two fiber webs, three fiber webs, four or more fiber webs) may form a fibrous layer. For instance, as illustrated in FIG. 1, a protective clothing material 5 may include a fibrous layer 10 comprising two nonwoven webs. Fibrous layer 10 may include a first nonwoven web 15 (e.g., meltblown fiber web) and a second nonwoven web 20 (e.g., meltblown fiber web). In some embodiments, the first and/or second nonwoven webs may comprise synthetic fibers. For instance the first and/or second nonwoven webs comprise continuous synthetic fibers formed, e.g., by a meltblowing process. In certain embodiments, first nonwoven web 15 may be directly adjacent to second nonwoven web 20 as shown in FIG. 1. As used herein, when a layer or fiber web is referred to as being "directly adjacent" to another layer or fiber web, it means that no intervening layer is present.

In some embodiments, first nonwoven web and second nonwoven web 20 may be joined (e.g., via a calendering process) to form a fibrous layer having beneficial properties. For instance, in some embodiments, fibrous layer 10 may have a relatively small mean flow pore size (e.g., greater than or equal to about 2 microns and less than or equal to about 5 microns) and/or maximum pore size (e.g., greater than or equal to about 6 microns and less than or equal to about 9 microns). The fibrous layer may also have a suitable basis weight (e.g., greater than or equal to about 20 g/m$^2$ and less than or equal to about 40 g/m$^2$). In some embodiments, fibrous layer 10 may be relatively lightweight, breathable, and/or permeable to air. For instance, fibrous layer 10 may have a relatively high air permeability (e.g., greater than or equal to about 4 CFM and less than or equal to about 10 CFM), and/or a relatively high moisture vapor transmission rate (e.g., greater than or equal to about 1,000 g/m$^2$ day). In certain embodiments, the fibrous layer may be relatively thin (e.g., greater than or equal to about 1 mil and less than or equal to about 6 mils).

In some embodiments, fibrous layer 10 may be relatively structurally uniform, such that the variance in or range of one or more structural properties when measured across the fibrous layer is relatively small. For instance, in some embodiments, the standard deviation in mean flow pore size when measured across the fibrous layer may be less than 1 micron. The difference between the maximum pore size and the mean flow pore size may be relatively small (e.g., greater than or equal to about 0 microns and less than or equal to about 10 microns). In some such embodiments, the ratio of mean flow pore size to maximum pore size may be greater than or equal to about 0.35 and less than or equal to about 0.55. In certain embodiments, the standard deviation in air permeability when measured across the fibrous layer may be less than 1 CFM.

Figure 2:
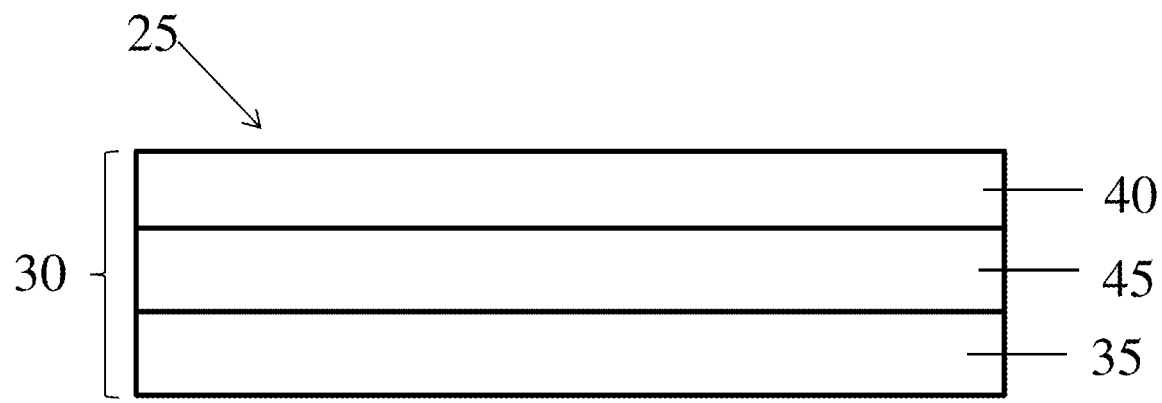
FIG. 2 is a schematic of a protective clothing material according to certain embodiments.

In some embodiments, three or more fiber webs may form a fibrous layer. For instance, as illustrated in FIG. 2, a protective clothing material 25 may comprise a fibrous layer 30 including a first nonwoven web 35, a second nonwoven web 40, and a third nonwoven web 45. The three nonwoven webs may be joined (e.g., via a calendering process) to form a fibrous layer having beneficial properties. In some embodiments, first nonwoven web 35, second nonwoven web 40, and/or third nonwoven web 45 may comprise synthetic fibers. In some such embodiments, the first nonwoven web, the second nonwoven web, and/or the third nonwoven web comprise continuous synthetic fibers formed, e.g., by a meltblowing or electrospinning process. For instance, first nonwoven web 35 and second nonwoven web 40 may be formed by a meltblowing process. In some such cases, third nonwoven web 45 may be formed by an electrospinning process. In other instances, third nonwoven web 45 may be formed by a meltblowing process. In certain embodiments, third nonwoven web 45 may be positioned between first nonwoven web 35 and second nonwoven web 40. In some such embodiments, third nonwoven web 45 may be directly adjacent to first nonwoven web 35 and/or second nonwoven web 40 as shown in FIG. 2. In other such embodiments, one or more intervening nonwoven webs may be positioned between third nonwoven web 45 and first nonwoven web 35 and/or second nonwoven web 40. Non-limiting examples of intervening nonwoven webs include meltspun webs (e.g., spunbond), centrifugal spun webs, solvent spun webs, electroblown webs, gel spun webs, and nonwoven webs comprising staple fibers.

Figure 3:
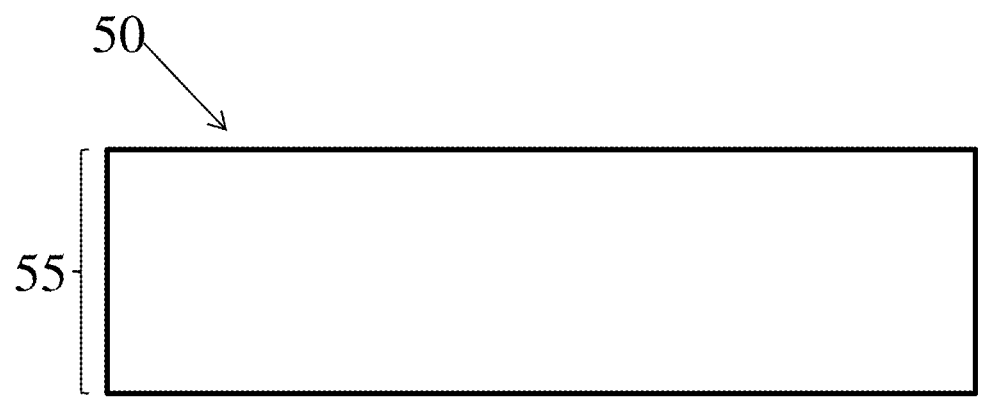
FIG. 3 is a schematic of a protective clothing material according to certain embodiments.

In other embodiments, the fibrous layer may include a single fiber web. For instance, as shown in FIG. 3, a protective clothing material 50 may include a fibrous layer 55 comprising a single nonwoven web (e.g., meltblown fiber web).

In general, the fibrous layer may comprise any suitable number of nonwoven webs (e.g., one nonwoven web, two nonwoven webs, three nonwoven webs, four nonwoven webs, five nonwoven webs, six or more nonwoven webs). Regardless of the number of nonwoven webs in the fibrous layer, the fibrous layer may have the properties described herein. For instance, in embodiments in which the fibrous layer comprises two or more nonwoven webs, the nonwoven webs may be joined (e.g., via a calendering process) to produce a fibrous layer having the properties described herein.

Regardless of the number of fiber webs in the fibrous layer, the protective clothing material may optionally comprise one or more coarse fiber layers. For instance, as described further below, the fibrous layer (e.g., a calendared fibrous layer) and one or more coarse fiber layers may be joined (e.g., via non-calendering process, via an adhesive) to impart beneficial properties to the protective clothing material. In some embodiments, the coarse fiber layers may include one or more nonwoven webs. In some embodiments, a coarse fiber layer may comprise a single nonwoven web (e.g., spunbond nonwoven web, carded nonwoven web, drylaid nonwoven web, wetlaid nonwoven web, spunlace nonwoven web). In other embodiments, the coarse fiber layer may comprise two or more nonwoven webs (e.g., two nonwoven webs, three nonwoven webs). In some embodiments, the coarse fiber layer may comprise fibers having a relatively large average diameter (e.g., greater than or equal to about 10 microns and less than or equal to about 50 microns). In certain embodiments, the coarse fiber layer may comprise synthetic fibers and/or natural fibers. For instance, a coarse fiber layer may comprise synthetic staple fibers.

Figure 4:
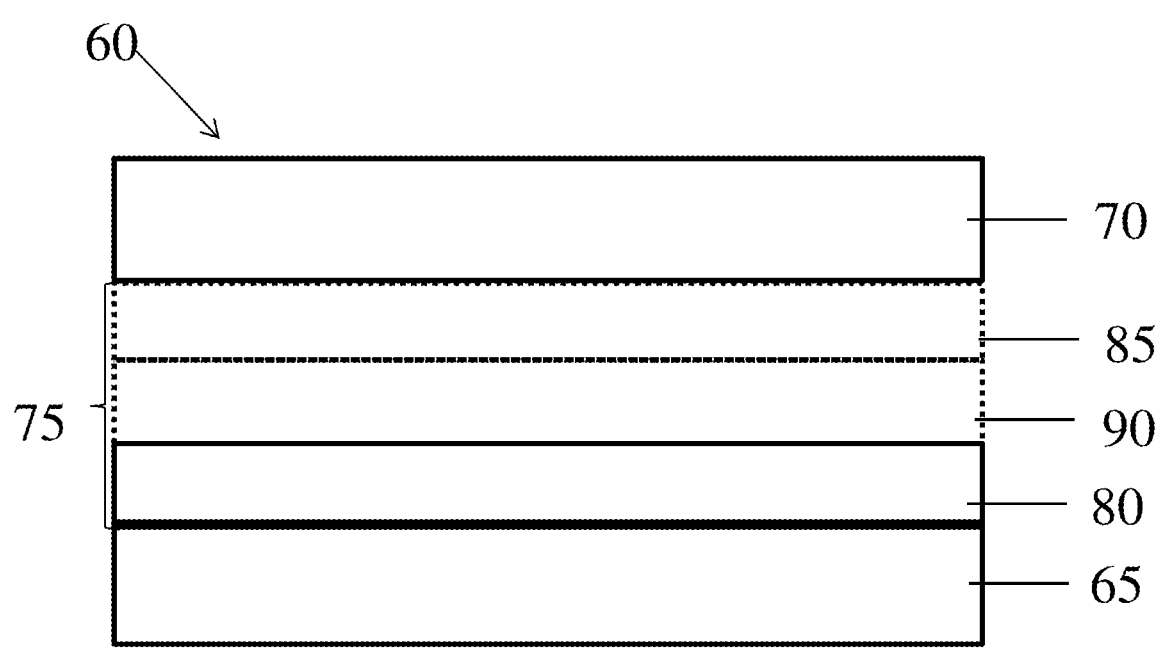
FIG. 4 is a schematic of a protective clothing material according to certain embodiments.

In some embodiments, as illustrated in FIG. 4, a protective clothing material 60 may include a first coarse fiber layer 65, a second coarse fiber layer 70, and a fibrous layer 75 comprising one or more nonwoven webs (e.g., 80, 85, and/or 90). The fibrous layer 75 may be positioned between first coarse fiber layer 65 and second coarse fiber layer 70. In some such embodiments, fibrous layer 75 may be directly adjacent to the first and/or second coarse fiber layer. In other such embodiments, one or more intervening nonwoven webs or layers, as described above, may be positioned between fibrous layer 75 and first coarse fiber layer 65 and/or second coarse fiber layer 70. Non-limiting examples of intervening nonwoven webs include meltspun webs (e.g., spunbond), centrifugal spun webs, solvent spun webs, electroblown webs, gel spun webs, and nonwoven webs comprising staple fibers. In certain embodiments, fibrous layer 75 may include a first nonwoven web (e.g., 80) and a second nonwoven web (e.g., 85). In some embodiments, fibrous layer 75 may include a third nonwoven web (e.g., 90) positioned between a first nonwoven web (e.g., 80) and a second nonwoven web (e.g., 85). In other embodiments, fibrous layer 75 may include a single fiber web (e.g., 80).

In some embodiments, first coarse fiber layer 65 and/or second coarse fiber layer 70 may be joined to fibrous layer 75, directly or indirectly. For example, first coarse fiber layer 65 and/or second coarse fiber layer 70 may be joined to fibrous layer 75 via an adhesive. For example, suitable adhesives include ethyl vinyl acetate (EVA), copolyesters, polyolefins, polyamides, polyurethanes, styrene block copolymers, thermoplastic elastomers, polycarbonates, silicones, and combinations thereof. In some instances, first coarse fiber layer 65 and/or second coarse fiber layer 70 may not be joined to fibrous layer 75 by a calendering process. In some such cases, first coarse fiber layer 65 and/or second coarse fiber layer 70 may not undergo a calendering process. For example, first coarse fiber layer 65 and/or second coarse fiber layer 70, in protective clothing material 60, may be uncalendered. In certain embodiments, fibrous layer 75 may be a calendered layer. In some such cases, fibrous layer 75 may be a calendered layer and first coarse fiber layer 65 and/or second coarse fiber layer 70 may be uncalendered layers. Protective coating materials having such constructions may have particularly beneficial properties.

In some embodiments, the protective clothing material may include one or more nonwoven webs or layers (e.g., coarse fiber layer, fibrous layer) having a portion (e.g., surface, interior, all) that repels a fluid (e.g., hydrophilic fluid, aqueous fluid, bodily fluid). In such cases, the nonwoven web or layer may substantially block the transport of droplets of the fluid across the protective clothing material. For example, the coarse fiber layer may repel fluid droplets (e.g., aqueous fluids, bodily fluids, hydrophilic fluids). As another example, the coarse fiber layer may repel droplets of a certain size and the fibrous layer may repel fluid droplets that are not repelled and/or removed by the coarse fiber layer. For instance, the fibrous layer may be designed to repel smaller droplets that bypass the coarse fibrous layer. In certain embodiments, the protective clothing material includes one or more nonwoven webs or layers (e.g., coarse fiber layer, fibrous layer) having a portion (e.g., surface, interior, all) that repels a hydrophilic fluid (e.g., aqueous fluid, bodily fluid). In some such embodiments, at least a portion of the nonwoven web or layer may be hydrophobic. For instance, the nonwoven web may comprise fibers formed from a hydrophobic material (e.g., polypropylene) and/or may be modified with a hydrophobic material.

In some embodiments, as described in more detail below, the protective clothing material may include one or more modified nonwoven webs or layers (e.g., surface modified fibrous layer, surface modified coarse layer, surface modified nonwoven web). In some such embodiments, at least a portion of the nonwoven web or layer (e.g., surface, interior, substantially all, entire) may be modified to repel a fluid (e.g., aqueous fluid, bodily fluid). For instance, the nonwoven web or layer may be modified to alter and/or reduce the wettability of at least a portion of the nonwoven web or layer (e.g., at least one surface of a layer) with respect to a particular fluid (e.g., to make a layer or nonwoven web more hydrophobic). For example, a hydrophobic surface having a water contact angle of 100° may be modified to have a water contact angle of greater than 100°, such as 130° or greater. In another example, a hydrophobic surface having a water contact angle of 100° may be modified to have a water contact angle of 150° or greater. In some embodiments, a surface with a contact angle greater than or equal to 150° C. may be referred to as a "superhydrophobic surface." A superhydrophobic surface may also have a low hysteresis of the contact angle.

As used herein, the terms "repel" and "repelling" may refer to the ability of a fluid to interact with the nonwoven web or layer, such that the contact angle of the fluid with respect to at least a portion (e.g., surface) of the nonwoven web or layer is greater than or equal to 90 degrees. As used herein, the terms "wettability" may refer to the ability of a fluid to interact with the nonwoven web or layer, such that the contact angle of the fluid with respect to at least a portion (e.g., surface) of the nonwoven web or layer is less than 90 degrees.

Figure 5A:
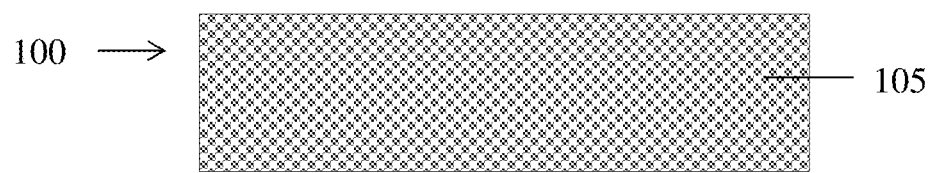
FIG. 5A is a schematic of a modified nonwoven web, according to one set of embodiments.
Figure 5B:
FIG. 5B is a schematic of a modified layer, according to certain embodiments.

Non-limiting examples of a modified nonwoven web and layer are shown in FIGS. 5A-B. As shown illustratively in FIG. 5A, at least a portion of a nonwoven web 100 (e.g., surface(s) and/or interior, entire nonwoven web) may be modified with a material 105. In some embodiments, at least a portion of the surface(s) of the nonwoven web (e.g., in the fibrous layer) may be modified with a material. For example, the nonwoven web may have one or more surfaces (e.g., outermost surface with respect to the protective clothing material, two opposing surfaces, the top surface and the bottom surface) modified with a material. In some cases, at least a portion of the interior of the nonwoven web may be modified with a material. In certain embodiments, at least a portion of the surface(s) and interior of the nonwoven web may be modified with a material. In some embodiments, the entire nonwoven web may be modified.

In some embodiments, as shown illustratively in FIG. 5B, at least a portion of a layer 110 (e.g., surface(s) and/or interior, entire layer) may be modified with a material 115. In some embodiments, at least a portion of the surface(s) of the layer (e.g., coarse fiber layer) may be modified with a material as illustrated in FIG. 5B. In certain embodiments, layer 110 may have two or more surfaces (e.g., two opposing surfaces, the top surface and the bottom surface) modified with a material. In other embodiments, layer 110 may have one surface (e.g., outermost surface with respect to the protective clothing material) modified with a material. In some cases, at least a portion of the interior of the layer may be modified with a material. In certain embodiments, at least a portion of the surface(s) and interior of the layer may be modified with a material In some embodiments, the entire layer may be modified.

In general, any suitable nonwoven web or layer in the protective clothing material may be a modified nonwoven web or layer. In some embodiments, the protective clothing material may comprise a single modified layer or nonwoven web. In some embodiments, each layer in the protective clothing material may be a modified layer. In certain embodiments, each nonwoven web in the protective clothing material may be a modified nonwoven web. In some embodiments, less than or equal to two nonwoven webs or layers in a protective clothing material may be modified. In some embodiments, the protective clothing material does not comprise a modified layer and/or nonwoven web.

As described herein, at least a portion of a nonwoven web or layer may be modified with a material. In certain embodiments, only a single surface of the nonwoven web or layer is modified with a material. In some instances, opposing surfaces of the nonwoven web or layer are modified with a material. In some cases, only the interior of the nonwoven web or layer is modified with a material. In some embodiments, the entire nonwoven web or layer may be modified with a material. In general, a modified layer or nonwoven web comprises a material on at least a portion of the fibers (e.g., at the surface, in the interior). In some cases, the material may form a coating on at least a portion of the fibers (e.g., at the surface, in the interior) of the layer or nonwoven web. In some embodiments, the material is not a binder resin or a portion of a multicomponent fiber.

In some embodiments, one or more nonwoven webs or layers in the protective clothing material may be designed to be discrete from another nonwoven web or layer. That is, the fibers from one nonwoven web or layer do not substantially intermingle (e.g., do not intermingle at all) with fibers from another nonwoven web or layer. For example, with respect to FIG. 1, in one set of embodiments, fibers from the first nonwoven web do not substantially intermingle with fibers of the second nonwoven web. As another example, fibers from the fibrous layer do not substantially intermingle with fibers of the optional coarse fiber layer. Discrete nonwoven webs and/or layers may be joined by any suitable process, such as calendering or by adhesives. For instance, in some embodiments, discrete nonwoven webs in the fibrous layer may be joined by calendering, as described in more detail below. In some such cases, a discrete fibrous layer may be joined to the optional coarse fiber layer(s) using adhesives. It should be appreciated, however, that certain embodiments may include one or more nonwoven webs or layers that are not discrete with respect to one another.

It should be understood that the configurations of the nonwoven webs and/or layers shown in the figures are by way of example only, and that in other embodiments, protective clothing materials including other configurations of nonwoven webs and/or layers may be possible. For example, while the first, optional second, and optional third nonwoven webs are shown in a specific order in FIG. 4, other configurations are also possible. For example, the optional second nonwoven web may be positioned between the first and third nonwoven webs. It should be appreciated that the terms "second" and "third" nonwoven webs or layers, as used herein, refer to different nonwoven webs or layers within the material, and are not meant to be limiting with respect to the location of that layer. Furthermore, in some embodiments, additional nonwoven webs or layers (e.g., "fourth", "fifth", "sixth", or "seventh" layers) may be present in addition to the ones shown in the figures. It should also be appreciated that not all components shown in the figures need be present in some embodiments.

As noted above, the fibrous layer may have a relatively small pore size. For instance, in some embodiments, the mean flow pore size of the fibrous layer may be less than or equal to about 6 microns, less than or equal to about 5.5 microns, less than or equal to about 5 microns, less than or equal to about 4.5 microns, less than or equal to about 4 microns, less than or equal to about 3.5 microns, less than or equal to about 3 microns, less than or equal to about 2.5 microns, less than or equal to about 2 microns, or less than or equal to about 1.5 microns. In some instances, the mean flow pore size may be greater than or equal to about 1 micron, greater than or equal to about 1.5 microns, greater than or equal to about 2 microns, greater than or equal to about 2.5 microns, greater than or equal to about 3 microns, greater than or equal to about 3.5 microns, greater than or equal to about 4 microns, greater than or equal to about 4.5 microns, greater than or equal to about 5 microns, or greater than or equal to about 5.5 microns. Combinations of the above-referenced ranges are also possible (e.g., greater than or equal to about 1 micron and less than or equal to about 6 microns, greater than or equal to about 2 microns and less than or equal to about 5 microns). The mean flow pore size may be determined according to the standard ASTM F316-03 (2011)

In some embodiments, the fibrous layer may have a relatively uniform mean flow pore size. For example, the standard deviation in mean flow pore size when measured across the fibrous layer may be relatively small. For instance, in some embodiments, the standard deviation in mean flow pore size when measured across the fibrous layer may be less than or equal to about 2 microns, less than or equal to about 1.8 microns, less than or equal to about 1.6 microns, less than or equal to about 1.4 microns, less than or equal to about 1.2 microns, less than or equal to about 1 micron, less than or equal to about 0.8 microns, less than or equal to about 0.6 microns, less than or equal to about 0.4 microns, less than or equal to about 0.2 microns, or less than or equal to about 0.1 microns. In some instances, the standard deviation in mean flow pore size may be greater than or equal to about 0 microns, greater than or equal to about 0.2 micron, greater than or equal to about 0.4 microns, greater than or equal to about 0.6 microns, greater than or equal to about 0.8 microns, greater than or equal to about 1 micron, greater than or equal to 1.2 about microns, greater than or equal to about 1.4 microns, greater than or equal to about 1.6 microns, or greater than or equal to about 1.8 microns. Combinations of the above-referenced ranges are also possible (e.g., greater than or equal to about 0 microns and less than or equal to about 2 microns, greater than or equal to about 0 micron and less than or equal to about 1 micron). The standard deviation in mean flow pore size may be determined according to the standard ASTM F316-03 (2011). Briefly, the mean flow pore size may be taken at regularly spaced intervals (e.g., 7 inches apart) along the width of the material. The standard deviation is determined from a statistically significant number of samples. For example, to determine the standard deviation of a fibrous layer and/or protective clothing material having an area of 1 m$^2$, a width of 2 m, and a length of 0.5 m, the mean flow pore size is measured at 12 locations along the width of the layer or material. The first measurement is taken 4 inches from an edge of the layer or material that is used to determine the width and the last measurement is taken 4 inches from the other edge used to determine the width. The remaining measurements are spaced across the width, such that the 12 measurements are approximately equidistant apart. The standard deviation is calculated using methods known to those of ordinary skill in the art.

In some embodiments, the maximum pore size of the fibrous layer may be relatively small. For instance, in some embodiments, the maximum pore size of the fibrous layer may be greater than or equal to about 4 microns, greater than or equal to about 5 microns, greater than or equal to about 6 microns, greater than or equal to about 7 microns, greater than or equal to about 8 microns, greater than or equal to about 9 microns, greater than or equal to about 10 microns, or greater than or equal to about 11 microns. In some instances, the maximum pore size of the fibrous layer may be less than or equal to about 12 microns, less than or equal to about 11 microns, less than or equal to about 10 microns, less than or equal to about 9 microns, less than or equal to about 8 microns, less than or equal to about 7 microns, less than or equal to about 6 microns, or less than or equal to about 5 microns. Combinations of the above-referenced ranges are also possible (e.g., greater than or equal to about 4 microns and less than or equal to about 12 microns, greater than or equal to about 6 microns and less than or equal to about 9 microns). The maximum pore size may be determined according to the standard ASTM F316-03 (2011).

In some embodiments, the ratio of mean flow pore size to maximum pore size of the fibrous layer may be greater than or equal to about 0.1, greater than or equal to about 0.2, greater than or equal to about 0.35, greater than or equal to about 0.4, greater than or equal to about 0.5, greater than or equal to about 0.6, greater than or equal to about 0.7, greater than or equal to about 0.8, or greater than or equal to about 0.9. In some instances, the ratio of a mean flow pore size to a maximum pore size may be less than or equal to about 1.0, less than or equal to about 0.9, less than or equal to about 0.8, less than or equal to about 0.7, less than or equal to about 0.6, less than or equal to about 0.55, less than or equal to about 0.4, less than or equal to about 0.3, or less than or equal to about 0.2. Combinations of the above-referenced ranges are also possible (e.g., greater than or equal to about 0.1 and less than or equal to about 1.0, or greater than or equal to about 0.35 and less than or equal to about 0.55). The ratio may be determined according to the standard ASTM F316-03 (2011).

In some embodiments, the difference between the mean flow pore size and the maximum pore size may be relatively small. For instance, in some embodiments, the difference between the mean flow pore size and the maximum pore size may be less than or equal to about 10 microns, less than or equal to about 9 microns, less than or equal to about 8 microns, less than or equal to about 7 microns, less than or equal to about 6 microns, less than or equal to about 5 microns, less than or equal to about 4 microns, less than or equal to about 3 microns, less than or equal to about 2 microns, or less than or equal to about 1 micron. In some instances, the difference may be greater than or equal to about 0 microns, greater than or equal to about 1 micron, greater than or equal to about 2 microns, greater than or equal to about 3 microns, greater than or equal to about 4 microns, greater than or equal to about 5 microns, greater than or equal to about 6 microns, greater than or equal to about 7 microns, greater than or equal to about 8 microns, or greater than or equal to about 9 microns. Combinations of the above-referenced ranges are also possible (e.g., greater than or equal to about 0 micron and less than or equal to about 10 microns, greater than or equal to about 0 microns and less than or equal to about 6 microns).

In some embodiments, the fibrous layer may have a relatively high air permeability. For instance, in some embodiments, the fibrous layer may have an air permeability of greater than or equal to about 1 ft$^3$/min (CFM), greater than or equal to about 2 CFM, greater than or equal to about 3 CFM, greater than or equal to about 4 CFM, greater than or equal to about 5 CFM, greater than or equal to about 6 CFM, greater than or equal to about 7 CFM, greater than or equal to about 8 CFM, or greater than or equal to about 9 CFM. In some instances, the air permeability of the fibrous layer may be less than or equal to 10 CFM, less than or equal to 9 CFM, less than or equal to about 8 CFM, less than or equal to 7 CFM, less than or equal to about 6 CFM, less than or equal to 5 CFM, less than or equal to about 4 CFM, less than or equal to 3 CFM, or less than or equal to 2 CFM. Combinations of the above-referenced ranges are also possible (e.g., greater than 1 CFM and less than or equal to 10 CFM, greater than 4 CFM and less than or equal to 10 CFM, greater than 4 CFM and less than or equal to 7 CFM). Other ranges are also possible. The air permeability may be determined using ASTM D737 (2016).

In some embodiments, the fibrous layer may have a relatively uniform air permeability. For example, the standard deviation in air permeability when measured across the fibrous layer may be relatively small. For instance, in some embodiments, the standard deviation in air permeability when measured across the fibrous layer may be less than or equal to about 2 CFM, less than or equal to about 1.8 CFM, less than or equal to about 1.6 CFM, less than or equal to about 1.5 CFM, less than or equal to about 1.3 CFM, less than or equal to about 1 CFM, less than or equal to about 0.8 CFM, less than or equal to about 0.6 CFM, less than or equal to about 0.5 CFM, less than or equal to about 0.3 CFM, or less than or equal to about 0.1 CFM. In some instances, the standard deviation in air permeability may be greater than or equal to about 0 CFM, greater than or equal to about 0.3 CFM, greater than or equal to about 0.5 CFM, greater than or equal to about 0.6 CFM, greater than or equal to about 0.8 CFM, greater than or equal to about 1 CFM, greater than or equal to 1.3 about CFM, greater than or equal to about 1.5 CFM, greater than or equal to about 1.6 CFM, or greater than or equal to about 1.8 CFM. Combinations of the above-referenced ranges are also possible (e.g., greater than or equal to about 0 CFM and less than or equal to about 2 CFM, greater than or equal to about 0 CFM and less than or equal to about 1 CFM). The standard deviation in air permeability may be determined according to the standard ASTM D737 (2016). Briefly, the mean flow pore size may be taken at regularly spaced intervals (e.g., 7 inches apart) along the width of the material. The standard deviation is determined from a statistically significant number of samples. For example, to determine the standard deviation of a fibrous layer and/or protective clothing material having an area of 1 $m^2$, a width of 2 m, and a length of 0.5 m, the mean flow pore size is measured at 12 locations along the width of the layer or material. The first measurement is taken 4 inches from an edge of the layer or material that is used to determine the width and the last measurement is taken 4 inches from the other edge used to determine the width. The remaining measurements are spaced across the width, such that the 12 measurements are approximately equidistant apart. The standard deviation is calculated using methods known to those of ordinary skill in the art.

In some embodiments, the fibrous layer may be relatively lightweight. For instance, in some embodiments, the fibrous layer for filtration may have a basis weight of less than or equal to about 50 $g/m^2$, less than or equal to about 45 $g/m^2$, less than or equal to about 40 $g/m^2$, less than or equal to about 35 $g/m^2$, less than or equal to about 30 $g/m^2$, less than or equal to about 25 $g/m^2$, less than or equal to about 20 $g/m^2$, or less than or equal to about 15 $g/m^2$. In some instances, the fibrous layer may have a basis weight of greater than or equal to about 10 $g/m^2$, greater than or equal to about 15 $g/m^2$, greater than or equal to about 20 $g/m^2$, greater than or equal to about 25 $g/m^2$, greater than or equal to about 30 $g/m^2$, greater than or equal to about 35 $g/m^2$, greater than or equal to about 40 $g/m^2$, or greater than or equal to about 45 $g/m^2$. Combinations of the above-referenced ranges are also possible (e.g., greater than or equal to about 10 $g/m^2$ and less than or equal to about 50 $g/m^2$, greater than or equal to about 20 $g/m^2$ and less than or equal to about 40 $g/m^2$). The basis weight may be determined according to the standard ASTM D3776 (2013).

In some embodiments, the fibrous layer may be relatively thin. For instance, in some embodiments, the thickness of the fibrous layer may be less than or equal to about 6 mils, less than or equal to about 5.5 mils, less than or equal to about 5 mils, less than or equal to about 4.5 mils, less than or equal to about 4 mils, less than or equal to about 3.5 mils, less than or equal to about 3 mils, less than or equal to about 2.5 mils, less than or equal to about 2 mils, or less than or equal to about 1.5 mils. In some instances, the thickness of the fibrous layer may be greater than or equal to about 1 mils, greater than or equal to about 1.5 mils, greater than or equal to about 2 mils, greater than or equal to about 2.5 mils, greater than or equal to about 3 mils, greater than or equal to about 3.5 mils, greater than or equal to about 4 mils, greater than or equal to about 4.5 mils, greater than or equal to about 5 mils, or greater than or equal to about 5.5 mils. Combinations of the above referenced ranges are also possible (e.g., greater than or equal to about 1 mils and less than or equal to about 6 mils, greater than or equal to about 2 mils and less than or equal to about 4 mils). The thickness may be determined according to the standard ASTM D1777 (2015) at 2.6 psi.

In some embodiments, the fibrous layer may be relatively breathable. For instance, in some embodiments, the fibrous layer may have a moisture vapor transmission rate of greater than or equal to about 100 $g/m^2$ day, greater than or equal to about 500 $g/m^2$ day, greater than or equal to about 1000 $g/m^2$ day, greater than or equal to about 2000 $g/m^2$ day, greater than or equal to about 3000 $g/m^2$ day, or greater than or equal to about 4000 $g/m^2$ day. In some embodiments, the fibrous layer may have a moisture vapor transmission rate of less than or equal to about 5000 $g/m^2$ day, less than or equal to about 4000 $g/m^2$ day, less than or equal to about 3000 $g/m^2$ day, less than or equal to about 2000 $g/m^2$ day, less than or equal to about 1000 $g/m^2$ day, or less than or equal to about 500 $g/m^2$ day. Combinations of the above-referenced ranges are also possible (e.g., greater than or equal to about 100 $g/m^2$ day and less than or equal to about 5000 $g/m^2$ day, or greater than or equal to about 1000 $g/m^2$ day and less than or equal to about 3000 $g/m^2$ day). The moisture vapor transmission rate may be determined according to the standard ASTM E96-16 (2016).

In some embodiments, fibrous layer and/or one or more nonwoven webs within the fibrous layer may comprise fibers having a relatively small average fiber diameter. For instance, in some embodiments, the average fiber diameter of the fibrous layer and/or one or more nonwoven webs within the fibrous layer may be less than or equal to about 10 microns, less than or equal to about 9 microns, less than or equal to about 8 microns, less than or equal to about 7 microns, less than or equal to about 6 microns, less than or equal to about 5 microns, less than or equal to about 4 microns, less than or equal to about 3 microns, less than or equal to about 2 microns, less than or equal to about 1.5 microns, less than or equal to about 1.0 microns, less than or equal to about 0.5 microns, or less than or equal to about 0.1 microns. In some instances, the average fiber diameter may be greater than or equal to about 0.01 microns, greater than or equal to about 0.05 microns, greater than or equal to about 0.10 microns, greater than or equal to about 0.2 microns, greater than or equal to about 0.5 microns, greater than or equal to about 0.7 microns, greater than or equal to about 1 micron, greater than or equal to about 2 microns, greater than or equal to about 3 microns, greater than or equal to about 4 microns, greater than or equal to about 5 microns, greater than or equal to about 6 microns, greater than or equal to about 7 microns, greater than or equal to about 8 microns, or greater than or equal to about 9 microns. Combinations of the above-referenced ranges are also possible (e.g., greater than or equal to about 0.01 microns and less than or equal to about 10 microns, greater than or equal to about 0.1 microns and less than or equal to about 10 microns, greater than or equal to about 0.05 microns and less than or equal to about 1.5 microns). In some embodiments, in which the fibrous layer comprises an electrospun nonwoven web, the average fiber diameter of the electrospun nonwoven web may be greater than or equal to about 0.01 microns and less than or equal to about 0.05 microns. The average fiber diameter may be determined using scanning electron microscopy. As used herein, fiber diameter refers to the largest cross-sectional dimension of the fiber from a cross-section perpendicular to the axis corresponding to the fiber length.

As described herein, in some embodiments, a protective clothing material may comprise one or more coarse fiber layers. For instance, the protective clothing material may comprise a fibrous layer positioned between and optionally adjacent to two coarse fiber layers. In some embodiments, the coarse fiber layer may be a relatively open layer that imparts splash resistance, breathability, and good air permeability to the protective clothing material. For instance, the coarse layer may prevent the transmission of low pressure liquids (e.g., spray of liquid, saliva). In some such embodiments, the coarse layer may repel hydrophilic fluids (e.g., bodily fluids). In some embodiments, the coarse layer may have a pore size and fiber diameter that impart breathability and good air permeability to the layer.

In some embodiments, the coarse fiber layer may be splash resistant. As used herein, the terms "splash resistant" (also referred to as spray impact resistant) and "splash resistance" (also referred to as spray impact resistance) have their ordinary meaning in the art and may refer to the ability of the layer to resist penetration of sprayed fluid. In some embodiments, the splash resistance of a layer and/or the protective clothing material may be determined using AATCC 42, which measures the resistance to the penetration of water by impact. Briefly, a 500 mL of deionized water is sprayed against a taut surface of a test specimen backed by a pre-weighed blotter using 2" diameter spray head having 25 holes at a height of 0.6 m. The test specimen backed by the pre-weighed blotter is angled at 45 degrees. The blotter is then reweighed to determine water penetration and the specimen is classified accordingly. If the difference in weight is less than 1.0 g, the specimen is splash resistant. In some embodiments, the difference in weight, according to this test, of the coarse fiber layer, fibrous layer, and/or protective clothing material may be less than 1.0 g (e.g., less than 0.8 g, less than 0.6 g, less than 0.3 g)

In some embodiments, the air permeability of the coarse fiber layer(s) may be greater than or equal to about 10 ft$^3$/min (CFM), greater than or equal to about 100 CFM, greater than or equal to about 250 CFM, greater than or equal to about 500 CFM, greater than or equal to about 750 CFM, greater than or equal to about 1000 CFM, greater than or equal to about 1250 CFM, greater than or equal to about 1500 CFM, or greater than or equal to about 1750 CFM. In some instances, the air permeability may be less than or equal to about 2000 CFM, less than or equal to about 1750 CFM, less than or equal to about 1500 CFM, less than or equal to about 1250 CFM, less than or equal to about 1000 CFM, less than or equal to about 750 CFM, less than or equal to about 500 CFM, less than or equal to about 250 CFM, or less than or equal to about 100 CFM. Combinations of the above-referenced ranges are also possible (e.g., greater than or equal to about 10 CFM and less than or equal to about 2000 CFM, greater than or equal to about 500 CFM and less than or equal to about 1000 CFM). The air permeability may be determined using ASTM D737 (2016).

In some embodiments, the coarse fiber layer(s) may have a relatively large pore size that contributes to the breathability and permeability of the protective clothing material. For instance, in some embodiments, the mean flow pore size of the coarse fiber layer(s) may be greater than or equal to about 100 microns, greater than or equal to about 200 microns, greater than or equal to about 300 microns, greater than or equal to about 400 microns, greater than or equal to about 500 microns, greater than or equal to about 600 microns, greater than or equal to about 700 microns, greater than or equal to about 800 microns, or greater than or equal to about 900 microns. In some instances, the mean flow pore size may be less than or equal to about 1000 microns, less than or equal to about 900 microns, less than or equal to about 800 microns, less than or equal to about 700 microns, less than or equal to about 600 microns, less than or equal to about 500 microns, less than or equal to about 400 microns, less than or equal to about 300 microns, or less than or equal to about 200 microns. Combinations of the above-referenced ranges are also possible (e.g., greater than or equal to about 100 microns and less than or equal to about 1000 microns, greater than or equal to about 400 microns and less than or equal to about 700 microns). The mean flow pore size may be determined according to the standard ASTM F316-03 (2011).

In some embodiments, the maximum pore size of the coarse fiber layer(s) may be greater than or equal to about 200 microns, greater than or equal to about 300 microns, greater than or equal to about 500 microns, greater than or equal to about 700 microns, greater than or equal to about 900 microns, greater than or equal to about 1000 microns, greater than or equal to about 1200 microns, greater than or equal to about 1400 microns, or greater than or equal to about 1600 microns. In some instances, the maximum pore size may be less than or equal to about 1800 microns, less than or equal to about 1600 microns, less than or equal to about 1400 microns, less than or equal to about 1200 microns, less than or equal to about 1000 microns, less than or equal to about 900 microns, less than or equal to about 700 microns, less than or equal to about 500 microns, or less than or equal to about 300 microns. Combinations of the above-referenced ranges are also possible (e.g., greater than or equal to about 200 microns and less than or equal to about 1800 microns, greater than or equal to about 500 microns and less than or equal to about 900 microns). The mean flow pore size may be determined according to the standard ASTM F316-03 (2011).

In some embodiments, the ratio of a mean flow pore size to a maximum pore size of the coarse fiber layer(s) may be greater than or equal to about 0.1, greater than or equal to about 0.2, greater than or equal to about 0.3, greater than or equal to about 0.4, greater than or equal to about 0.5, greater than or equal to about 0.6, greater than or equal to about 0.7, greater than or equal to about 0.8, or greater than or equal to about 0.9. In some embodiments, the ratio of mean flow pore size to the maximum pore size may be less than or equal to about 1.0, less than or equal to about 0.9, less than or equal to about 0.8, less than or equal to about 0.7, less than or equal to about 0.6, less than or equal to about 0.5, less than or equal to about 0.4, less than or equal to about 0.3, or less than or equal to about 0.2. Combinations of the above-referenced ranges are also possible (e.g., greater than or equal to about 0.1 and less than or equal to about 1.0, greater than or equal to about 0.5 and less than or equal to about 0.9). The ratio may be determined according to the standard ASTM F316-03 (2011).

In some embodiments, the coarse fiber layer(s) may comprise fibers having a relatively large fiber diameter that contribute to the breathability of the protective clothing material. For instance, in some embodiments, the average fiber diameter of the coarse fiber layer(s) may be greater than or equal to about 10 microns, greater than or equal to about 15 microns, greater than or equal to about 18 microns, greater than or equal to about 20 microns, greater than or equal to about 24 microns, greater than or equal to about 27 microns, greater than or equal to about 30 microns, greater than or equal to about 35 microns, greater than or equal to about 40 microns, or greater than or equal to about 45 microns. In some instances, the average fiber diameter may be less than or equal to about 50 microns, less than or equal to about 45 microns, less than or equal to about 40 microns, less than or equal to about 35 microns, less than or equal to about 30 microns, less than or equal to about 27 microns, less than or equal to about 24 microns, less than or equal to about 21 microns, or less than or equal to about 18 microns. Combinations of the above-referenced ranges are also possible (e.g., greater than or equal to about 10 microns and less than or equal to about 50 microns, greater than or equal to about 15 microns and less than or equal to about 30 microns).

In some embodiments, the coarse fiber layer(s) may have a basis weight of greater than or equal to about 5 g/m$^2$, greater than or equal to about 10 g/m$^2$, greater than or equal to about 15 g/m$^2$, greater than or equal to about 20 g/m$^2$, greater than or equal to about 25 g/m$^2$, greater than or equal to about 30 g/m$^2$, greater than or equal to about 35 g/m$^2$, greater than or equal to about 40 g/m$^2$, greater than or equal to about 45 g/m$^2$, greater than or equal to about 50 g/m$^2$, greater than or equal to about 55 g/m$^2$, greater than or equal to about 60 g/m$^2$, greater than or equal to about 65 g/m$^2$, greater than or equal to about 70 g/m$^2$, greater than or equal to about 75 g/m$^2$, greater than or equal to about 80 g/m$^2$, or greater than or equal to about 90 g/m$^2$. In some instances, the basis weight may be less than or equal to about 100 g/m$^2$, less than or equal to about 90 g/m$^2$, less than or equal to about 80 g/m$^2$, less than or equal to about 75 g/m$^2$, less than or equal to about 70 g/m$^2$, less than or equal to about 65 g/m$^2$, less than or equal to about 60 g/m$^2$, less than or equal to about 55 g/m$^2$, less than or equal to about 50 g/m$^2$, less than or equal to about 45 g/m$^2$, less than or equal to about 40 g/m$^2$, less than or equal to about 35 g/m$^2$, less than or equal to about 30 g/m$^2$, less than or equal to about 25 g/m$^2$, or less than or equal to about 20 g/m$^2$. Combinations of the above-referenced ranges are also possible (e.g., greater than or equal to about 5 g/m$^2$ and less than or equal to about 100 g/m$^2$, greater than or equal to about 15 g/m$^2$ and less than or equal to about 35 g/m$^2$).

As described herein, protective clothing material comprising a fibrous layer and optionally one or more coarse fiber layers may be particularly useful for a wide variety of applications, including the formation of ANSI/AAMI level 4 protective garments (e.g., surgical gowns, surgical hoods). In some embodiments, the protective clothing material may have the requisite protection rating and good wearability (e.g., comfort). For instance, in some embodiments, the protective clothing material and/or the fibrous layer may pass the ASTM F1671-13 Method B (i.e., viral penetration) and ASTM F1670-08(2014) e1 Method (i.e., synthetic blood penetration) test required for ANSI/AAMI level 4 certification.

In addition to a high protection rating, the protective clothing material may also have a relatively high air permeability. For instance, in some embodiments, the protective clothing material may have an air permeability of greater than or equal to about 1 CFM, greater than or equal to about 2 CFM, greater than or equal to about 3 CFM, greater than or equal to about 4 CFM, greater than or equal to about 5 CFM, greater than or equal to about 6 CFM, greater than or equal to about 7 CFM, greater than or equal to about 8 CFM, or greater than or equal to about 9 CFM. In some instances, the air permeability may be less than or equal to about 10 CFM, less than or equal to about 9 CFM, less than or equal to about 8 CFM, less than or equal to about 7 CFM, less than or equal to about 6 CFM, less than or equal to about 5 CFM, less than or equal to about 4 CFM, less than or equal to about 3 CFM, or less than or equal to about 2 CFM. All combinations of the above-referenced ranges are possible (e.g., greater than about 1 CFM and less than or equal to about 10 CFM, greater than about 4 CFM and less than or equal to about 7 CFM). The air permeability may be determined according to the standard ASTM D737 (2016).

In some embodiments, the protective clothing material may be relatively breathable. For instance, in some embodiments, the protective clothing material may have a moisture vapor transmission rate of greater than or equal to about 100 g/m$^2$ day, greater than or equal to about 500 g/m$^2$ day, greater than or equal to about 1000 g/m$^2$ day, greater than or equal to about 2000 g/m$^2$ day, greater than or equal to about 3000 g/m$^2$ day, or greater than or equal to about 4000 g/m$^2$ day. In some embodiments, the protective clothing material may have a moisture vapor transmission rate of less than or equal to about 5000 g/m$^2$ day, less than or equal to about 4000 g/m$^2$ day, less than or equal to about 3000 g/m$^2$ day, less than or equal to about 2000 g/m$^2$ day, less than or equal to about 1000 g/m$^2$ day, or less than or equal to about 500 g/m$^2$ day. Combinations of the above-referenced ranges are also possible (e.g., greater than or equal to about 100 g/m$^2$ day and less than or equal to about 5000 g/m$^2$ day, or greater than or equal to about 1000 g/m$^2$ day and less than or equal to about 3000 g/m$^2$ day). The moisture vapor transmission rate may be determined according to the standard ASTM E-96-16.

In some embodiments, the protective clothing material may be relatively lightweight. For instance, in some embodiments, the protective clothing material may have a basis weight of greater than or equal to about 10 g/m$^2$, greater than or equal to about 20 g/m$^2$, greater than or equal to about 30 g/m$^2$, greater than or equal to about 40 g/m$^2$, greater than or equal to about 50 g/m$^2$, greater than or equal to about 60 g/m$^2$, greater than or equal to about 70 g/m$^2$, greater than or equal to about 80 g/m$^2$, or greater than or equal to about 90 g/m$^2$. In some instances, the protective clothing material may have a basis weight of less than or equal to about 100 g/m$^2$, less than or equal to about 90 g/m$^2$, less than or equal to about 80 g/m$^2$, less than or equal to about 70 g/m$^2$, less than or equal to about 60 g/m$^2$, less than or equal to about 50 g/m$^2$, less than or equal to about 40 g/m$^2$, less than or equal to about 30 g/m$^2$, or less than or equal to about 20 g/m$^2$. Combinations of the above-referenced ranges are also possible (e.g., greater than or equal to about 10 g/m$^2$ and less than or equal to about 100 g/m$^2$, greater than or equal to about 40 g/m$^2$ and less than or equal to about 70 g/m$^2$). The basis weight may be determined according to the standard ASTM D3776 (2013).

In some embodiments, the protective clothing material may be relatively thin. For instance, in some embodiments, the thickness of the protective clothing material may be less than or equal to about 20 mils, less than or equal to about 18 mils, less than or equal to about 15 mils, less than or equal to about 12 mils, less than or equal to about 10 mils, less than or equal to about 9 mils, less than or equal to about 7 mils, or less than or equal to about 6 mils. In some instances, the thickness may be greater than or equal to about 5 mils, greater than or equal to about 7 mils, greater than or equal to about 9 mils, greater than or equal to about 10 mils, greater than or equal to about 12 mils, greater than or equal to about 15 mils, or greater than or equal to about 18 mils. Combinations of the above referenced ranges are also possible (e.g., greater than or equal to about 5 mils and less than or equal to about 20 mils, greater than or equal to about 10 mils and less than or equal to about 15 mils). The thickness may be determined according to the standard ASTM D1777 (2015) at 2.6 psi.

In some embodiments, the protective clothing material may have a relatively a relatively small mean flow and/or maximum pore sizes. For instance, in some embodiments, the protective clothing material has a mean flow pore size of less than or equal to about 5 microns, less than or equal to about 4.5 microns, less than or equal to about 4 microns, less than or equal to about 3.5 microns, less than or equal to about 3 microns, less than or equal to about 2.5 microns, less than or equal to about 2 microns, or less than or equal to about 1.5 microns. In some instances, the protective clothing material may have a mean flow pore size of greater than or equal to about 1 micron, greater than or equal to about 1.5 microns, greater than or equal to about 2 microns, greater than or equal to about 2.5 microns, greater than or equal to about 3 microns, greater than or equal to about 3.5 microns, greater than or equal to about 4 microns, or greater than or equal to about 4.5 microns. Combinations of the above-referenced ranges are also possible (e.g., greater than or equal to about 1 micron and less than or equal to about 5 microns, greater than or equal to about 1.5 microns and less than or equal to about 3 microns). The mean flow pore size may be determined according to the standard ASTM F316-03 (2011).

In some embodiments, the protective clothing material has a maximum pore size of less than or equal to about 10 microns, less than or equal to about 9 microns, less than or equal to about 8 microns, less than or equal to about 7 microns, less than or equal to about 6 microns, less than or equal to about 5 microns, less than or equal to about 4 microns, or less than or equal to about 3 microns. In some instances, the protective clothing material may have a maximum pore size of greater than or equal to about 2 microns, greater than or equal to about 3 microns, greater than or equal to about 4 microns, greater than or equal to about 5 microns, greater than or equal to about 6 microns, greater than or equal to about 7 microns, greater than or equal to about 8 microns, or greater than or equal to about 9 microns. Combinations of the above-referenced ranges are also possible (e.g., greater than or equal to about 2 microns and less than or equal to about 10 microns, greater than or equal to about 4 microns and less than or equal to about 7 microns). The mean flow pore size may be determined according to the standard ASTM F316-03 (2011).

In some embodiments, the protective clothing material may have a suitable Mullen Burst strength for use in a protective garment. For instance, in some embodiments, protective clothing material may have a Mullen Burst strength of greater than or equal to about 30 psi, greater than or equal to about 35 psi, greater than or equal to about 40 psi, greater than or equal to about 45 psi, greater than or equal to about 50 psi, or greater than or equal to about 55 psi. In some instances, the Mullen Burst strength may be less than or equal to about 60 psi, less than or equal to about 55 psi, less than or equal to about 50 psi, less than or equal to about 45 psi, less than or equal to about 40 psi, or less than or equal to about 35 psi. Combinations of the above-referenced ranges are also possible (e.g., greater than or equal to about 30 psi and less than or equal to about 60 psi). The Mullen Burst strength may be determined according to the standard ASTM D774 (2010).

In some embodiments, the hydrostatic pressure or hydrostatic head range of the protective clothing material and/or the fibrous layer may be relatively high (e.g., greater than or equal to about 100 cm $H_2O$). For instance, in some embodiments, the hydrostatic pressure or hydrostatic head range of the protective clothing material and/or the fibrous layer may greater than or equal to about 50 cm $H_2O$, greater than or equal to about 75 cm $H_2O$, greater than or equal to about 100 cm $H_2O$, greater than or equal to about 125 cm $H_2O$, greater than or equal to about 150 cm $H_2O$, greater than or equal to about 175 cm $H_2O$, greater than or equal to about 200 cm $H_2O$, greater than or equal to about 225 cm $H_2O$, greater than or equal to about 250 cm $H_2O$, or greater than or equal to about 275 cm $H_2O$. In some instances, the hydrostatic pressure or hydrostatic head range may be less than or equal to about 300 cm $H_2O$, less than or equal to about 275 cm $H_2O$, less than or equal to about 250 cm $H_2O$, less than or equal to about 225 cm $H_2O$, less than or equal to about 200 cm $H_2O$, less than or equal to about 175 cm $H_2O$, less than or equal to about 150 cm $H_2O$, less than or equal to about 125 cm $H_2O$, or less than or equal to about 100 cm $H_2O$. Combinations of the above-referenced ranges are possible (e.g., greater than or equal to about 50 cm $H_2O$ and less than or equal to about 300 cm $H_2O$, greater than or equal to about 100 cm $H_2O$ and less than or equal to about 200 cm $H_2O$)

In some embodiments, the weight percentage of the fibrous layer in the protective clothing material may be greater than or equal to about 1%, greater than or equal to about 10%, greater than or equal to about 20%, greater than or equal to about 30%, greater than or equal to about 40%, greater than or equal to about 50%, greater than or equal to about 60%, greater than or equal to about 70%, or greater than or equal to about 80%. In some instances, the weight percentage of the fibrous layer in the protective clothing material may be less than or equal to about 99%, less than or equal to about 80%, less than or equal to about 70%, less than or equal to about 60%, less than or equal to about 50%, less than or equal to about 40%, less than or equal to about 30%, less than or equal to about 20%, or less than or equal to about 10%. Combinations of the above-referenced ranges are also possible (e.g., greater than or equal to about 1% and less than or equal to about 99%, greater than or equal to about 40% and less than or equal to about 60%).

In some embodiments, the weight percentage of the coarse fiber layer(s) in the protective clothing material may be greater than or equal to about 1%, greater than or equal to about 10%, greater than or equal to about 20%, greater than or equal to about 30%, greater than or equal to about 40%, greater than or equal to about 50%, greater than or equal to about 60%, greater than or equal to about 70%, or greater than or equal to about 80%. In some instances, the weight percentage of the coarse fiber layer(s) in the protective clothing material may be less than or equal to about 99%, less than or equal to about 80%, less than or equal to about 70%, less than or equal to about 60%, less than or equal to about 50%, less than or equal to about 40%, less than or equal to about 30%, less than or equal to about 20%, or less than or equal to about 10%. Combinations of the above-referenced ranges are also possible (e.g., greater than or equal to about 1% and less than or equal to about 99%, greater than or equal to about 40% and less than or equal to about 60%).

In general, the contact angle of one or more nonwoven webs, one or more layers (e.g., coarse fiber layer), and/or the protective clothing material may be selected to repel a fluid (e.g., hydrophilic fluid). In some embodiments, the water contact angle on a surface of one or more nonwoven webs, one or more layers, and/or the protective clothing material may be greater than 90 degrees, greater than or equal to 100 degrees, greater than or equal to 105 degrees, greater than or equal to 110 degrees, greater than or equal to 115 degrees, greater than or equal to 120 degrees, greater than or equal to 125 degrees, greater than or equal to 130 degrees, greater than or equal to 135 degrees, greater than or equal to 145 degrees, greater than or equal to 150 degrees, greater than or equal to 155 degrees, or greater than or equal to 160 degrees. In some instances, the water contact angle is less than or equal to about 165 degrees, less than or equal to about 160 degrees, less than or equal to about 150 degrees, less than or equal to about 140 degrees, less than or equal to about 130 degrees, less than or equal to about 120 degrees, less than or equal to about 110 degrees, or less than or equal to about 100 degrees. Combinations of the above-referenced ranges are also possible (e.g., greater than or equal to about 90 degrees and less than or equal to about 165 degrees). The water contact angle may be measured using standard ASTM D5946 (2009). The contact angle is the angle between the substrate surface and the tangent line drawn to the water droplet surface at the three-phase point, when a liquid drop is resting on the substrate surface. A contact angle meter or goniometer can be used for this determination.

As described herein, one or more layers (e.g., fibrous layer, coarse fiber layer), one or more nonwoven webs, and/or the protective clothing material may comprise synthetic fibers. In some instances, one or more layers (e.g., fibrous layer, coarse fiber layer), one or more nonwoven webs, and/or the entire protective clothing material may comprise a relatively high weight percentage of synthetic fibers (e.g., greater than or equal to about 95 wt. %, 100 wt. %). In some instances, the fibrous layer may comprise a relatively high weight percentage of synthetic fibers (e.g., greater than or equal to about 95 wt. %, 100 wt. %). In some instances, the synthetic fibers may be continuous (e.g., greater than about 10 cm, greater than about 50 cm, greater than about 200 cm), as described further below. In certain embodiments, one or more nonwoven webs (e.g., first nonwoven web, second nonwoven web) may comprise a relatively high percentage (e.g., greater than or equal to about 95 wt. %, 100 wt. %) of synthetic fibers (e.g., meltblown fibers, electrospun fibers). In certain embodiments, one or more coarse fiber layers (e.g., first coarse fiber layer, second coarse fiber layer) may comprise a relatively high percentage (e.g., greater than or equal to about 75 wt. %, greater than or equal to about 95 wt. %, 100 wt. %) of synthetic fibers (e.g., synthetic staple fibers).

In some embodiments, the fibers in one or more nonwoven webs, the layers (e.g., fibrous layer), and/or the protective clothing material may be continuous fibers formed by any suitable process (e.g., a meltblowing, a meltspinning, an electrospinning, centrifugal spinning). In certain embodiments, at least some of the synthetic fibers may be formed by a meltblowing or electrospinning process (e.g., melt electrospinning, solvent electrospinning). In other embodiments, the synthetic fibers may be non-continuous. In some embodiments, all of the fibers in the protective clothing material are synthetic fibers. In certain embodiments, all of the fibers in the fibrous layer are synthetic fibers.

In some cases, the synthetic fibers may be continuous (e.g., electrospun fibers, meltblown fibers, spunbond fibers, centrifugal spun fibers, etc.). For instance, synthetic fibers may have an average length of at least about 10 cm, at least about 15 cm, at least about 20 cm, at least about 50 cm, at least about 100 cm, at least about 200 cm, at least about 500 cm, at least about 700 cm, at least about 1000 cm, at least about 1500 cm, at least about 2000 cm, at least about 2500 cm, at least about 5000 cm, at least about 10000 cm; and/or less than or equal to about 10000 cm, less than or equal to about 5000 cm, less than or equal to about 2500 cm, less than or equal to about 2000 cm, less than or equal to about 1000 cm, less than or equal to about 500 cm, or less than or equal to about 200 cm. Combinations of the above-referenced ranges are also possible (e.g., greater than or equal to about 100 cm and less than or equal to about 2500 cm). Other values of average fiber length are also possible.

In other embodiments, the synthetic fibers (e.g., in the coarse fiber layer(s)) are not continuous (e.g., staple fibers). In general, synthetic non-continuous fibers may be characterized as being shorter than continuous synthetic fibers. For instance, in some embodiments, synthetic fibers may have an average length of greater than or equal to about 1 mm, greater than or equal to about 4 mm, greater than or equal to about 6 mm, greater than or equal to about 10 mm, greater than or equal to about 15 mm, greater than or equal to about 20 mm, greater than or equal to about 25 mm, greater than or equal to about 30 mm, greater than or equal to about 35 mm, greater than or equal to about 40 mm, greater than or equal to about 50 mm, greater than or equal to about 60 mm, greater than or equal to about 70 mm, greater than or equal to about 80 mm, greater than or equal to about 90 mm. In some instances, the average length may be less than or equal to about 100 mm, less than or equal to about 80 mm, less than or equal to about 60 mm, less than or equal to about 40 mm, less than or equal to about 30 mm, less than or equal to about 20 mm, less than or equal to about 15 mm, or less than or equal to about 10 mm. Combinations of the above-referenced ranges are also possible (e.g., at least about 1.0 mm and less than or equal to about 100 mm, at least about 6.0 mm and less than or equal to about 30 mm).

In some embodiments in which synthetic fibers are included in the protective clothing material, the weight percentage of synthetic fibers in one or more layers, one or more nonwoven webs, and/or the protective clothing material may be greater than or equal to about 50%, greater than or equal to about 60%, greater than or equal to about 75%, greater than or equal to about 90%, greater than or equal to about 95%, greater than or equal to about 98%, or greater than or equal to about 99%. In some instances, the weight percentage of synthetic fibers may be less than or equal to about 100%, less than or equal to about 99%, less than or equal to about 98%, less than or equal to about 95%, less than or equal to about 90%, less than or equal to about 80%, or less than or equal to about 70%. Combinations of the above-referenced ranges are also possible (e.g., greater than or equal to about 75% and less than or equal to about 100%). In some embodiments, one or more nonwoven webs, one or more layers (e.g., fibrous layer, coarse fiber layer), and/or the protective clothing material includes 100% synthetic fibers.

Synthetic fibers may include any suitable type of synthetic polymer. Examples of suitable synthetic fibers include polyimide, aliphatic polyamide (e.g., nylon 6), aromatic polyamide, polysulfone, cellulose acetate, polyether sulfone, polyaryl ether sulfone, modified polysulfone polymers, modified polyethersulfone polymers, polymethyl methacrylate, polyacrylonitrile, polyurethane, poly(urea urethane), polybenzimidazole, polyetherimide, polyacrylonitrile, poly(ethylene terephthalate), polypropylene, silicon dioxide (silica), regenerated cellulose (e.g., Lyocell, rayon,) carbon (e.g., derived from the pyrolysis of polyacrilonitrile), polyaniline, poly(ethylene oxide), poly(ethylene naphthalate), poly(butylene terephthalate), styrene butadiene rubber, polystyrene, poly(vinyl chloride), poly(vinyl alcohol), poly(vinylidene fluoride), poly(ethylene-co-vinyl acetate), polyethyleneoxide, chitosan, polyhydroxybutyrate, hydroxyapatite, fiberglass, poly(vinyl butylene) and copolymers or derivative compounds thereof, and combinations thereof. In some embodiments, the synthetic fibers are hydrophobic. In some embodiments, the synthetic fibers are organic polymer fibers. Synthetic fibers may also include multi-component fibers (i.e., fibers having multiple components such as bicomponent fibers). In some cases, synthetic fibers may include electrospun (e.g., melt, solvent), meltblown, meltspun, or centrifugal spun fibers, which may be formed of polymers described herein (e.g., polyester, polypropylene). In some embodiments, synthetic fibers may be electrospun fibers. In some embodiments, synthetic fibers may be meltblown fibers. The filter media, as well as each of the fiber webs within the filter media, may also include combinations of more than one type of synthetic fiber.

In certain embodiments, a protective clothing material comprising two or more layers including fibers formed from the same or similar material may have beneficial properties during seaming and/or at the seams. For instance, protective garments formed from a protective clothing material comprising two or more layers including fibers formed from the same or similar material can be formed using heat sealing and/or ultrasonic seaming. In some cases, protective garments formed from such a protective clothing material may have seams that have the same protection rating as the rest of the garment. Conversely, protective garments formed from a protective clothing material comprising two or more layers including dissimilar material may not be amenable to seaming via heat sealing and/or ultrasonic seaming. In such cases, thread may be used to join protective clothing material together to form a garment. The seams containing thread may have a lower protection rating than the rest of the garment.

In some embodiments, two or more layers in the protective clothing material may comprise fibers formed from the same or similar material (e.g., synthetic polymer). For instance, the fibrous layer may include synthetic fibers including a certain synthetic polymer (e.g., polypropylene) and the coarse fiber layer(s) may include synthetic fibers including the same synthetic polymer (polypropylene). As another example, two or more nonwoven webs in the fibrous layer may comprise synthetic fibers including the same synthetic polymer (e.g., polypropylene). In some embodiments, the weight percentage of fibers in a layer that include the same or similar material (e.g., synthetic polymer) as fibers in another layer (e.g., adjacent layer) may be relatively high (e.g., greater than or equal to about 80 wt. %, greater than or equal to about 85 wt. %, greater than or equal to about 90 wt. %, greater than or equal to about 95 wt. %, 100 wt. %). In certain embodiments, the weight percentage of fibers in a layer that include a different material (e.g., synthetic polymer) than fibers in another layer (e.g., adjacent layer) may be relatively low (e.g., less than or equal to about 20 wt. %, less than or equal to about 15 wt. %, less than or equal to about 10 wt. %, less than or equal to about 5 wt. %). In some embodiments, one or more nonwoven webs (e.g., first nonwoven web, second nonwoven web), one or more layers (e.g., coarse fiber layer, fibrous layers) and/or the entire protective clothing material may include a single fiber type (e.g., synthetic fibers). For example, the coarse fiber layer(s) and fibrous layer may include only polypropylene fibers.

In general, the protective clothing material, and accordingly the fibrous layer and coarse fiber layer, may include any suitable fiber type. For instance, in some embodiments, the coarse fiber layer(s) may include natural fibers (e.g., cotton fibers, cellulose fibers) that are, e.g., comfortable for the wearer. In some such embodiments, one or more coarse fiber layers may include a blend of synthetic fibers (e.g., rayon fibers, acrylic fibers) and natural fibers (e.g., cotton fibers) A carded blend of synthetic and natural fibers (like cotton).

Protective clothing materials, described herein, may comprise layers produced using any suitable processes, such as a non-wet laid or a wet laid process. In some embodiments, one or more nonwoven webs (e.g., in the fibrous layer) and/or one or more layers (e.g., coarse fiber layer) may be produced using a non-wet laid process, such as blowing or spinning process. In some embodiments, one or more nonwoven webs (e.g., in the fibrous layer), one or more layers, and/or the entire protective clothing material may be formed by a meltblowing system, such as the meltblown system described in U.S. Publication No. 2009/0120048, filed Nov. 7, 2008, and entitled "Meltblown Filter Medium", and U.S. Publication No. 2012-0152824, filed Dec. 17, 2010, and entitled, "Fine Fiber Filter Media and Processes", each of which is incorporated herein by reference in its entirety for all purposes. In certain embodiments, one or more nonwoven webs and/or one or more layers may be formed by a meltspinning or a centrifugal spinning process.

In some embodiments, the nonwoven webs and/or layers, described herein, may have a relatively low amount of or essentially no process defects. In general, it is believed that subjecting the polymer composition used to form the fibers in the nonwoven web to relatively high temperatures and pressures for extended periods of time in an extrusion system can cause the polymer composition to degrade. Degradation may involve chain scission, i.e., shortening of the polymer chains to produce lower molecular weight polymers, and/or other forms of decomposition (e.g., chemical decomposition, thermal decomposition, ionization). As a result of polymer degradation, small polymeric particles may be formed. These particles may have the same chemical composition as the polymer composition used to form the fibers (but having a lower molecular weight), or may be a derivative of the polymer composition used to form the fibers. The particles may be associated with the nonwoven web in various configurations. For instance, the particles may reside on the surface of the fibers, on the surface of the fiber web, in the center of the fiber web, or in combinations thereof.

The shape and size of the polymeric particles formed may vary, and in some cases, the particles can even agglomerate to form larger particles. It should be understood that the polymeric particles described herein are different from fibers. The polymeric particles are non-fibrous, and generally have an aspect ratio (i.e., a length to largest cross-sectional dimension) of less than 50:1 and a largest cross-sectional dimension of at least 0.2 mm. For instance, in some embodiments, a particle may have a largest cross-sectional dimension of less than or equal to about 10 mm, less than or equal to about 8 mm, less than or equal to about 6 mm, less than or equal to about 4 mm, less than or equal to about 2 mm, less than or equal to about 1 mm, or less than or equal to about 0.5 mm. In some instances, a particle may have a largest cross-sectional dimension of greater than or equal to about 0.2 mm, greater than or equal to about 0.5 mm, greater than or equal to about 1.0 mm, greater than or equal to about 2.0 mm, greater than or equal to about 4.0 mm, greater than or equal to about 6.0 mm, greater than or equal to about 8.0 mm. It should be understood that all combinations of the above-referenced ranges are possible (e.g., greater than or equal to about 0.2 mm and less than or equal to about 10 mm). Other values and ranges of particle size are also possible.

In certain embodiments, the number average molecular weight of the particles formed during a fiber extrusion process may be less than or equal to about ½ the number average molecular weight of the polymer used to form the fibers. For instance, the number average molecular weight of the particles formed during a fiber extrusion process may be less than or equal to about ⅛, less than or equal to about 1/64, or less than or equal to about 1/200 the number average molecular weight of the polymer used to form the fibers. Other values of molecular weight of the particles associated with a fiber web are also possible.

In some embodiments, a nonwoven web and/or layer as described herein may include a relatively low number of or essentially no particles (e.g., on its surface). The amount of particles may be measured by determining the surface density of particles on the nonwoven web, i.e., the number of particles on a surface of the nonwoven web per unit area of the nonwoven web surface. For instance, a nonwoven web and/or layer may have a surface density of particles of less than or equal to about 12.0 particles/inch$^2$, less than or equal to about 10.0 particles/inch$^2$, less than or equal to about 8.0 particles/inch$^2$, less than or equal to about 6.0 particles/inch$^2$, less than or equal to about 4.0 particles/inch$^2$, less than or equal to about 2.5 particles/inch$^2$, less than or equal to about 2.2 particles/inch$^2$, less than or equal to about 2.0 particles/inch$^2$, less than or equal to about 1.8 particles/inch$^2$, less than or equal to about 1.6 particles/inch$^2$, less than or equal to about 1.5 particles/inch$^2$, less than or equal to about 1.3 particles/inch$^2$, less than or equal to about 1.0 particles/inch$^2$, less than or equal to about 0.8 particles/inch$^2$, less than or equal to about 0.5 particles/inch$^2$, or less than or equal to about 0.3 particles/inch$^2$, wherein each of the particles has a largest cross-sectional dimension of one of the ranges or values described above. For example, in one particular embodiment, a nonwoven web and/or layer has a surface density of particles of less than or equal to about 3.0 particles/inch$^2$, wherein each of the particles has a largest cross-sectional dimension of about 0.2 mm or greater. In this embodiment, even though the nonwoven web may include some particles having a largest cross-sectional dimension smaller than about 0.2 mm, these particles are not accounted for in calculating the surface density of particles. In another embodiment, a nonwoven web and/or layer has a surface density of particles of less than or equal to about 3.0 particles/inch$^2$, wherein each of the particles has a largest cross-sectional dimension of about 1.0 mm or greater. In this embodiment, even though the nonwoven web and/or layer may include some particles having a largest cross-sectional dimension smaller than about 1.0 mm, these particles are not accounted for in calculating the surface density of particles. Other surface densities of particles in a particular size range or value are also possible.

The number of particles per unit area of nonwoven web and/or layer can be determined as follows. A sample of nonwoven web and/or layer can be layered together with carbon paper and a white sheet of standard copy paper, where the carbon paper is positioned between the nonwoven web and the copy paper. The composite structure can be placed in a continuous belt press where the following conditions are employed: a line speed of 2.5 m/min, a pressure of 6 bars, and a temperature of about 68° F.-80° F. (room temperature). After exposure to these conditions, the degraded polymer particles, if present, may lie at an elevated position compared to the fibers, and appear as small "dots" on the underlying copy paper. If a darker image is needed for detection, the copy paper can be photocopied with a standard copier to darken the carbon image. This copy paper image can be scanned using standard imaging software, and software (e.g., ImageJ software available for download at http://rsbweb.nih.gov/ij/) can be used to determine the number of "dots" on the image. These "dots" may be measured in pixels, and each pixel can be correlated to a certain size to determine the size and number of particles. For instance, 1 pixel may correspond to 0.2646 mm, so a "dot" having a size of 1 pixel on the image may correspond to 1 particle having a largest dimension of 0.2646 mm; a "dot" having a size of 4 pixels on the image may correspond to 1 particle having a largest dimension of 1.1 mm. Pixel sizes may vary depending on the imaging hardware and/or software used. To calculate a surface density of particles, wherein each of the particles has a largest cross-sectional dimension of, for example, about 1.0 mm or greater, only the "dots" having a size of at least 4 pixels (e.g., a largest cross-sectional dimension of about 1.0 mm or greater) would be counted. This number would be divided by the area of the nonwoven web and/or layer used for counting the particles to determine the surface density of particles. In this particular instance, even though the nonwoven web and/or layer may include some particles having a largest cross-sectional dimension smaller than about 1.0 mm, these particles are not accounted for the purpose of this particular calculation.

Methods of forming nonwoven webs and/or layers having a relatively low number of or essentially no defects (e.g., particles on one or more surfaces of the web) are described in more detail in U.S. Publication No. 2012-0152824, filed Dec. 17, 2010, and entitled, "Fine Fiber Filter Media and Processes".

In some embodiments, one or more nonwoven webs (e.g., in the fibrous layer) and/or one or more layers may be formed by an electrospinning process. In some embodiments, electrospinning utilizes a high voltage differential to generate a fine jet of polymer solution from bulk polymer solution. The jet forms as the polymer is charged by the potential and electrostatic repulsion forces overcome the surface tension of the solution. The jet gets drawn into a fine fiber under the effect of repulsive electrical forces applied to the solution. The jet dries in flight and is collected on a grounded collector. The rapid solvent evaporation during this process leads to the formation of polymeric nanofiber which are randomly arranged into a web. In some embodiments, electrospun fibers are made using non-melt fiberization processes. Electrospun fibers can be made with any suitable polymers including but not limiting to, organic polymers, inorganic material (e.g., silica), hybrid polymers, and any combination thereof. In some embodiments, the synthetic fibers, described herein, may be formed from an electrospinning process.

In some embodiments, a non-wet laid process, such as an air laid or carding process, may be used to form one or more nonwoven webs and/or one or more layers (e.g., coarse fiber layer). For example, in an air laid process, synthetic fibers may be mixed, while air is blown onto a conveyor. In a carding process, in some embodiments, the fibers are manipulated by rollers and extensions (e.g., hooks, needles) associated with the rollers. In some embodiments, one or more coarse fiber layers may be formed from a carding process. In some cases, forming the nonwoven webs through a non-wet laid process may be more suitable for the production of a highly porous media. In some embodiments, a blowing or spinning process may be used to form the nonwoven webs in the fibrous layer and another non-wetlaid process (e.g., carding) may be used to form one or more coarse fiber layers (e.g., two coarse fiber layers).

In some embodiments, one or more nonwoven webs and/or one or more layers (e.g., coarse fiber layer) may be produced using a wet laid process. In general, a wet laid process involves mixing together of fibers of one or more type; for example, polymeric staple fibers of one type may be mixed together with polymeric staple fibers of another type, and/or with fibers of a different type (e.g., synthetic fibers and/or natural fibers), to provide a fiber slurry. The slurry may be, for example, aqueous-based slurry. In certain embodiments, fibers, are optionally stored separately, or in combination, in various holding tanks prior to being mixed together (e.g., to achieve a greater degree of uniformity in the mixture).

During or after formation of a nonwoven web and/or coarse fiber layer, the nonwoven web and/or coarse fiber layer may be further processed according to a variety of known techniques. In some embodiments, one or more nonwoven webs may be further processed to form the fibrous layer. For example, two or more nonwoven webs may be formed separately and combined by any suitable method (e.g., calendering) to form the fibrous layer. The two or more nonwoven webs may be formed using different processes (e.g., electrospinning, meltblowing), or the same process (e.g., meltbowing). For instance, each of the nonwoven webs may be independently formed by a non-wet laid process (e.g., meltblown process, melt spinning process, centrifugal spinning process, electrospinning process, dry laid process, air laid process), a wet laid process, or any other suitable process.

In general, further processing of one or more nonwoven webs to form the fibrous layer may alter one or more properties of the nonwoven web(s). In some such embodiments, the fibrous layer may have different properties than the nonwoven web(s) used to form the layer. For instance, the fibrous layer may be more structurally uniform, have a smaller pore size (e.g., mean flow pore size, maximum pore size), have a smaller air permeability, and/or a larger basis weight than the nonwoven web(s) used to form the fibrous layer. For example, one or more nonwoven webs used to form the fibrous layer may have a mean flow pore size of greater than or equal to about 1 micron and less than or equal to about 30 microns (e.g., greater than or equal to about 8 microns and less than or equal to about 15 microns) whereas the fibrous layer may have a mean flow pore size of greater than or equal to about 1 micron and less than or equal to about 6 microns (e.g., greater than or equal to about 2 microns and less than or equal to about 5 microns). One or more nonwoven webs used to form the fibrous layer may have a maximum pore size of greater than or equal to about 10 microns and less than or equal to about 35 microns (e.g., greater than or equal to about 15 microns and less than or equal to about 25 microns) whereas the fibrous layer may have a maximum pore size of greater than or equal to about 4 microns and less than or equal to about 12 microns (e.g., greater than or equal to about 6 microns and less than or equal to about 9 microns). As another example, one or more nonwoven webs used to form the fibrous layer may have an air permeability of greater than or equal to about 10 CFM and less than or equal to about 150 CFM (e.g., greater than or equal to about 40 CFM and less than or equal to about 100 CFM) whereas the fibrous layer may have an air permeability of greater than or equal to about 1 CFM and less than or equal to about 10 CFM (e.g., greater than or equal to about 4 CFM and less than or equal to about 10 CFM). One or more nonwoven webs used to form the fibrous layer may have a basis weight of greater than or equal to about 5 $g/m^2$ and less than or equal to about 25 $g/m^2$ (e.g., greater than or equal to about 10 $g/m^2$ and less than or equal to about 20 $g/m^2$) whereas the fibrous layer may have a basis weight of greater than or equal to about 10 $g/m^2$ and less than or equal to about 50 $g/m^2$ (e.g., greater than or equal to about 20 $g/m^2$ and less than or equal to about 40 $g/m^2$). In one example, one or more nonwoven webs used to form the fibrous layer may have a thickness of greater than or equal to about 1 mil and less than or equal to about 7 mils (e.g., greater than or equal to about 4 mils and less than or equal to about 6 mils) whereas the fibrous layer may have a thickness of greater than or equal to about 1 mil and less than or equal to about 6 mils (e.g., greater than or equal to about 2 mils and less than or equal to about 4 mils). In general, the further processing step used to form the fibrous layer may impart beneficial properties to the fibrous layer, such as a relatively high protection rating (e.g., ANSI/AAMI level 4).

In some embodiments, one or more nonwoven webs may undergo a calendering step to form the fibrous layer having different properties than the nonwoven web(s) used to form the layer. In certain embodiments, substantially all the nonwoven webs in the fibrous layer may undergo a calendering process. In some such embodiments in which the fibrous layer is formed from two or more nonwoven webs, the nonwoven webs may be calendered together. In general, calendering may involve, for example, compressing a single nonwoven web or two or more nonwoven webs (e.g., first and second nonwoven webs) together using calender rolls under a particular pressure, temperature, and line speed.

In general, the pressure, temperature, and line speed of the calendering process may be selected to make the fibers plastic and/or change the shape of the fibers (e.g., from cylindrical to ribbon-like) without significantly changing the absolute value of the diameter of the fibers. For example, the calendaring process may change the absolute value of the average diameter of the fibers by less than or equal to about 0.3 microns (e.g., less than or equal to about 0.2 microns). For instance, the temperature during calendering may be less than the melting temperature of one or more of the polymers (e.g., one polymer, all polymers) in the nonwoven web(s). For example, when the nonwoven web(s) comprise polypropylene fibers, the calendering temperature may be less than the melting temperature of the polypropylene fibers. In certain embodiments, the temperature may be less than or equal to about 100° C., less than or equal to about 95° C., less than or equal to about 90° C., or less than or equal to about 85° C. and/or greater than or equal to about 75° C. In some embodiments, a relatively high calendering pressure may be used. For instance, the pressure may be greater than or equal to about 450 pounds per linear inch (e.g., greater than or equal to about 700 pli). In some embodiments, the pressure may be between about 450 pli to about 900 pli (e.g., between about 700 pli to about 900 pli). The line speed may be between about 5 ft/min to about 100 ft/min (e.g., between about 5 ft/min to about 80 ft/min, between about 10 ft/min to about 50 ft/min, between about 15 ft/min to about 100 ft/min, or between about 20 ft/min to about 90 ft/min).

In other embodiments, one or more layers may be uncalendered. For example, one or more coarse layers may not undergo a calendering process and may be combined to the fibrous layer using another process (e.g., by adhesives).

Non-limiting examples of other further processing steps include lamination, co-pleating, and collation. In some embodiments, a further processing step may be used to add additional nonwoven webs to a layer and/or the protective clothing material. As described herein, in some embodiments two or more nonwoven webs and/or two or more layers of the protective clothing material may be formed separately and combined by any suitable method (such as lamination, calendering, collation), or by use of adhesives which may be preferred in certain cases. In some such embodiments, two or more layers may be formed using different processes (e.g., meltblowing, carding), or the same process (e.g., meltblowing). For example, each of the layers may be independently formed by a non-wet laid process (e.g., meltblown process, melt spinning process (e.g., spunbond process), centrifugal spinning process, electrospinning process, dry laid process, air laid process).

As noted above, in some embodiments, the fibrous layer and coarse fiber layer(s) may be combined using an adhesive. For instance, the layers (e.g., fibrous layer and coarse fiber layer(s)) may be adhered using adhesives, such that the layers (e.g., fibrous layer and coarse fiber layer(s)) are adhesively bound. In some of these embodiments, the fibrous layer is calendered and subsequently combined with the coarse fiber layer(s) (e.g., two coarse fiber layers) using an adhesive. In such embodiments, the coarse fiber layer(s) may be uncalendered. Such a construction may exhibit particularly attractive properties, for example, as compared to constructions that include similar layers that are combined entirely using a calendering process. Non-limiting examples of suitable adhesives include ethyl vinyl acetate (EVA), copolyesters, polyolefins, polyamides, polyurethanes, styrene block copolymers, thermoplastic elastomers, polycarbonates, silicones, and combinations thereof. Adhesives can be applied using different methods like spray coating (solution spraying if solvent or water based adhesives are used or melt spraying if hot melt adhesive is used), dip coating, kiss roll, knife coating, and gravure coating.

Lamination may involve, for example, compressing two or more webs together using a flatbed laminator or any other suitable device at a particular pressure and temperature for a certain residence time (i.e., the amount of time spent under pressure and heat). For instance, the pressure may be between about 5 psi to about 150 psi (e.g., between about 30 psi to about 90 psi, between about 60 psi to about 120 psi, between about 30 and 60 psi, or between about 90 psi and about 120 psi); the temperature may be between about 75° F. and about 400° F. (e.g., between about 75° F. and about 300° F., between about 200° F. and about 350° F., or between about 275° F. and about 390° F.); and the residence time between about 1 second to about 60 seconds (e.g., between about 1 second to about 30 seconds, between about 10 second to about 25 seconds, or between about 20 seconds and about 40 seconds). Other ranges for pressure, temperature, and residence time are also possible.

In some embodiments, the one or more nonwoven webs may include one or more additives (e.g., a lubricant, a slip agent, a surfactant, a coupling agent, a crosslinking agent). In certain instances, one or more additives can be used to reduce or eliminate the number of polymeric particles formed on or in the nonwoven web(s).

As noted above, in some embodiments, one or more nonwoven webs, one or more layers (e.g., coarse fiber layer, fibrous layer), and/or the protective clothing material may be modified with a material. In general, any suitable method for modifying the surface and/or the interior of a nonwoven web, layer, or protective clothing material may be used, such as melt additives and coating. In some embodiments, the surface and/or interior of a nonwoven web, layer, or protective clothing material may be modified by coating at least a portion of the surface and/or interior. In certain embodiments, a coating process involves introducing resin or a material (e.g., hydrophobic material) dispersed in a solvent or solvent mixture onto a pre-formed nonwoven web, layer, or protective clothing material (e.g., a pre-formed nonwoven web formed by a wetlaid process, meltblown process, etc.). Non-limiting examples of coating methods include the use of vapor deposition (e.g., chemical vapor, physical vapor deposition), layer-by-layer deposition, wax-solidification, self-assembly, sol-gel processing, a slot die coater, gravure coating, screen coating, size press coating (e.g., a two roll-type or a metering blade type size press coater), film press coating, blade coating, roll-blade coating, air knife coating, roll coating, foam application, reverse roll coating, bar coating, curtain coating, champlex coating, brush coating, Bill-blade coating, short dwell-blade coating, lip coating, gate roll coating, gate roll size press coating, laboratory size press coating, melt coating, dip coating, knife roll coating, spin coating, spray coating (e.g., electrospraying), gapped roll coating, roll transfer coating, padding saturant coating, and saturation impregnation. Other coating methods are also possible. In some embodiments, the material (e.g., hydrophobic material) may be applied to the nonwoven web using a non-compressive coating technique. The non-compressive coating technique may coat the nonwoven web, while not substantially decreasing the thickness of the web. In other embodiments, the resin may be applied to the nonwoven web using a compressive coating technique.

In one set of embodiments, a surface and/or interior of a nonwoven web, layer, or protective clothing material is modified using chemical vapor deposition, e.g., at least a portion of a surface of, interior of, and/or an entire nonwoven web, layer, or protective clothing material may comprise a chemical vapor deposition coating. In chemical vapor deposition, the nonwoven web is exposed to gaseous reactants from gas or liquid vapor that are deposited onto the nonwoven web under high energy level excitation such as thermal, microwave, UV, electron beam or plasma. Optionally, a carrier gas such as oxygen, helium, argon and/or nitrogen may be used.

Other vapor deposition methods include atmospheric pressure chemical vapor deposition (APCVD), low pressure chemical vapor deposition (LPCVD), metal-organic chemical vapor deposition (MOCVD), plasma assisted chemical vapor deposition (PACVD) or plasma enhanced chemical vapor deposition (PECVD), laser chemical vapor deposition (LCVD), photochemical vapor deposition (PCVD), chemical vapor infiltration (CVI) and chemical beam epitaxy (CBE).

In physical vapor deposition (PVD) thin films are deposited by the condensation of a vaporized form of the desired film material onto substrate. This method involves physical processes such as high-temperature vacuum evaporation with subsequent condensation, or plasma sputter bombardment rather than a chemical reaction.

After applying the coating to the nonwoven web, layer, or protective clothing material, the coating may be dried by any suitable method. Non-limiting examples of drying methods include the use of a photo dryer, infrared dryer, hot air oven steam-heated cylinder, or any suitable type of dryer familiar to those of ordinary skill in the art.

In some embodiments, at least a portion of the fibers of a nonwoven web, layer, or protective clothing material may be modified (e.g., coated) without substantially blocking the pores of the nonwoven web. In some instances, substantially all of the fibers may be coated without substantially blocking the pores. In some embodiments, the nonwoven web, layer, or protective clothing material may be coated with a relatively high weight percentage of resin or material without blocking the pores of a nonwoven web, layer, or protective clothing material using the methods described herein (e.g., by dissolving and/or suspending one or more material in a solvent to form the resin).

In some cases, a melt additive may be incorporated into at least a portion of the fibers in a nonwoven web, layer, and/or protective clothing material to modify the nonwoven web, layer, and/or protective clothing material. For example, in certain embodiments, a melt additive may be used to modify the hydrophobicity of at least a surface of the nonwoven web, layer, and/or protective clothing material.

In some cases, the melt additive may comprise a preblended masterbatch melt additive. Preblended masterbatch melt additives are known in the art and one of ordinary skill would be capable of incorporating preblended masterbatch melt additives into fibers based upon the teachings of this specification. A preblended masterbatch melt additive may be used to make hydrophobic fibers, which may be used to make at least a portion of the nonwoven webs, layers, and/or protective clothing materials hydrophobic.

In general, any suitable material may be used to alter the chemistry (e.g., surface chemistry), and accordingly the wettability, of a nonwoven web, layer, or protective clothing material.

In general, the net charge of the modified portion of nonwoven web, layer, or protective clothing material (e.g., surface, interior) may be negative, positive, or neutral. In some embodiments, the nonwoven web, layer, or protective clothing material (e.g., surface) may be modified with an electrostatically neutral material.

In some embodiments, small molecules may be used to modify at least one surface and/or interior of a nonwoven web, layer, or protective clothing material. In certain embodiments, the small molecule may be an inorganic or organic hydrophobic molecule. Non-limiting examples include hydrocarbons (e.g., $CH_4$, $C_2H_2$, $C_2H_4$, $C_6H_6$), fluorocarbons (e.g., $CF_4$, $C_2F_4$, $C_3F_6$, $C_3F_8$, $C_4H_8$, $C_5H_{12}$, $C_6F_6$), silanes (e.g., $SiH_4$, $Si_2H_6$, $Si_3H_8$, $Si_4H_{10}$), organosilanes (e.g., methylsilane, dimethylsilane, triethylsilane), siloxanes (e.g., dimethylsiloxane, hexamethyldisiloxane), ZnS, CuSe, InS, CdS, tungsten, silicon carbide, silicon nitride, silicon oxynitride, titanium nitride, carbon, silicon-germanium, and hydrophobic acrylic monomers terminating with alkyl groups and their halogenated derivatives (e.g., ethyl 2-ethylacrylate, methyl methacrylate; acrylonitrile). In certain embodiments, suitable hydrocarbons for modifying a surface of a layer may have the formula $C_xH_y$, where x is an integer from 1 to 10 and y is an integer from 2 to 22. In certain embodiments, suitable silanes for modifying a surface of a layer may have the formula $Si_nH_{2n+2}$ where any hydrogen may be substituted for a halogen (e.g., Cl, F, Br, I), and where n is an integer from 1 to 10.

As used herein, "small molecules" refers to molecules, whether naturally-occurring or artificially created (e.g., via chemical synthesis) that have a relatively low molecular weight. Typically, a small molecule is an organic compound (i.e., it contains carbon). The small organic molecule may contain multiple carbon-carbon bonds, stereocenters, and other functional groups (e.g., amines, hydroxyl, carbonyls, and heterocyclic rings, etc.). In certain embodiments, the molecular weight of a small molecule is at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and at most about 500 g/mol) are also possible.

In some embodiments, polymers may be used to modify at least one surface and/or interior of a nonwoven web, layer, or protective clothing material. For example, one or more polymers may be applied to at least a portion of a surface and/or interior of a nonwoven web, layer, or protective clothing material via a coating technique. In certain embodiments, the polymer may be formed from monobasic carboxylic acids and/or unsaturated dicarboxylic (dibasic) acids. In certain embodiments, the polymer may be a graft copolymer and may be formed by grafting polymers or oligomers to polymers in the fibers and/or nonwoven web (e.g., resin polymer). The graft polymer or oligomer may comprise carboxyl moieties that can be used to form a chemical bond between the graft and polymers in the fibers and/or nonwoven web. Non-limiting examples of polymers in the fibers and/or nonwoven web that can be used to form a graft copolymer include polyethylene, polypropylene, polycarbonate, polyvinyl chloride, polytetrafluoroethylene, polystyrene, cellulose, polyethylene terephthalate, polybutylene terephthalate, and nylon, and combinations thereof. Graft polymerization can be initiated through chemical and/or radiochemical (e.g., electron beam, plasma, corona discharge, UV-irradiation) methods.

In some embodiments, a gas may be used to modify at least one surface and/or interior of a nonwoven web, layer, or protective clothing material. In some such cases, the molecules in the gas may react with material (e.g., fibers, resin, additives) on the surface of a nonwoven web, layer, or protective clothing material to form functional groups, such as charged moieties, and/or to increase the oxygen content on the surface of the layer. Non-limiting examples of functional groups include hydroxyl, carbonyl, ether, ketone, aldehyde, acid, amide, acetate, phosphate, sulfite, sulfate, amine, nitrile, and nitro groups. Non-limiting examples of gases that may be reacted with at least one surface of a layer (e.g., modified) includes $CO_2$, $SO_2$, $SO_3$, $NH_3$, $N_2H_4$, $N_2$, $H_2$, He, Ar, and air, and combinations thereof.

The protective clothing material may include any suitable number of nonwoven webs, e.g., at least 2, at least 3, at least 4, at least 5, at least 6, at least 7, at least 8, or at least 10 nonwoven webs. In some embodiments, the protective clothing material may include up to 20 nonwoven webs.

In some embodiments, a layer described herein may be or include a nonwoven web. A nonwoven web may include non-oriented fibers (e.g., a random arrangement of fibers within the web). Examples of nonwoven webs include webs made by wet-laid or non-wet laid processes as described herein.

The protective clothing material may be incorporated into a variety of protective garments for use in various environments including operating rooms or anywhere else ANSI/AAMI level 4 protective garments are needed. The protective clothing material may be used to form surgical apparel (e.g., surgical hoods, surgical gown). The term "surgical apparel" has its ordinary meaning in the art and may be in accordance with the 21 C.F.R. § 878.4040(a) (2012). For example, surgical apparel may be a device that is intended to be worn by operating room personnel during surgical procedures to protect both the surgical patient and the operating room personnel from transfer of microorganisms, body fluids, and particulate material. Non-limiting examples include surgical caps, hoods, masks, gowns, operating room shoes and shoe covers, and isolation masks and gowns. In certain embodiments, the protective clothing material may be used to form surgical drapes. The term "surgical drape" has its ordinary meaning in the art and may be in accordance with the 21 C.F.R. § 878.4370(a) (2012). For example, a surgical drape may be a device made of natural or synthetic materials intended to be used as a protective patient covering, such as to isolate a site of surgical incision from microbial and other contamination. In certain embodiments, the device may include a plastic wound protector that may adhere to the skin around a surgical incision or be placed in a wound to cover its exposed edges. In some instances, the device may include a self-retaining finger cot that is intended to allow repeated insertion of the surgeon's finger into the rectum during performance of a transurethral prostatectomy. One of ordinary skill in the art would be knowledgeable about methods of forming surgical garments from protective clothing material. In general, the protective clothing material is cut and sewn together as in traditional garment manufacturing, except heat sealing and/or ultrasonic seaming are used instead of traditional sewing techniques involving thread. Heat sealing or ultrasonic seaming is used to form a good seal (e.g., impermeable seal), while maintaining the integrity of the garment and barrier protection.

During use, the protective clothing materials mechanically trap contaminants (e.g., bodily fluid, microbes) and prevents strikethrough. The protective clothing materials need not be electrically charged to enhance trapping of contamination. Thus, in some embodiments, the protective clothing materials are not electrically charged. However, in some embodiments, the protective clothing materials may be electrically charged.

EXAMPLES

Example 1

This example describes a protective clothing material including a calendered layer positioned between two coarse fiber nonwoven webs. The protective clothing material had a ANSI/AAMI level 4 protection rating, a high air permeability, low basis weight, and uniform structural properties. A protective clothing material containing a first coarse fiber nonwoven web, a calendered layer including two nonwoven webs, and a second coarse fiber nonwoven web was formed. The calendered layer was directly adjacent to the first and second coarse fiber nonwoven webs.

Figure 6A:
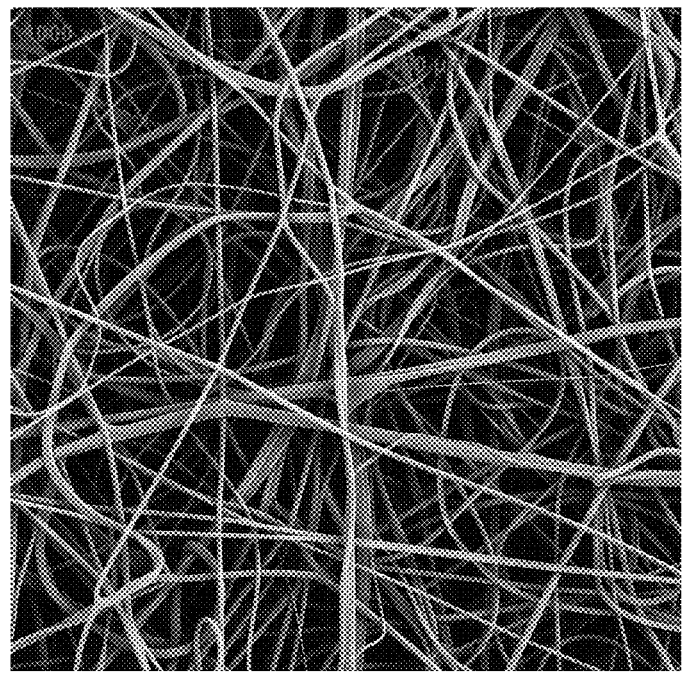
FIG. 6A is scanning electron microscope images of a fibrous layer before calendering (top) and after calendering (bottom) according to one set of embodiments.
Figure 6A:
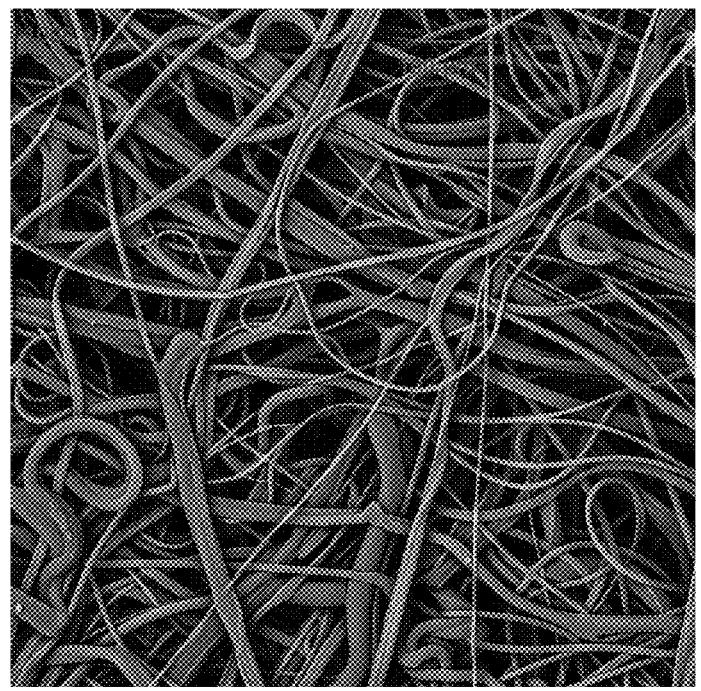
Figure 6B:
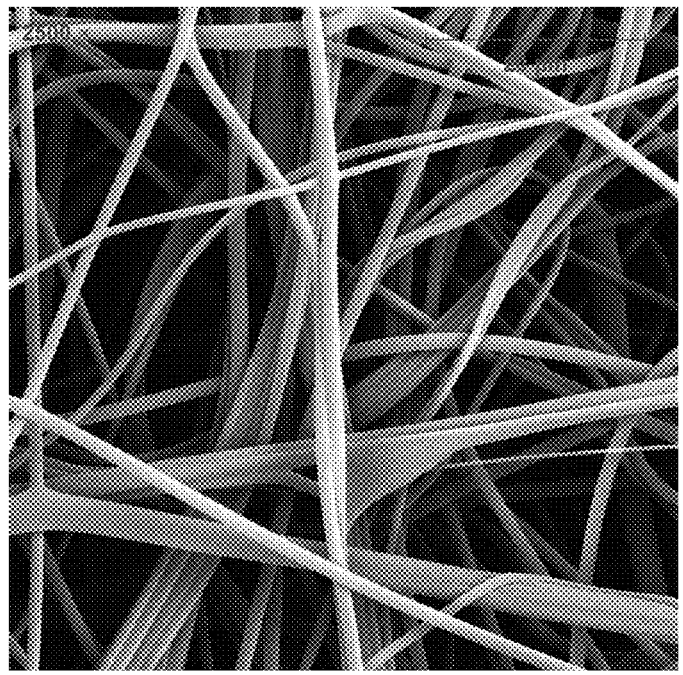
FIG. 6B is scanning electron microscope images of a fibrous layer before calendering (top) and after calendering (bottom) according to one set of embodiments.
Figure 6B:
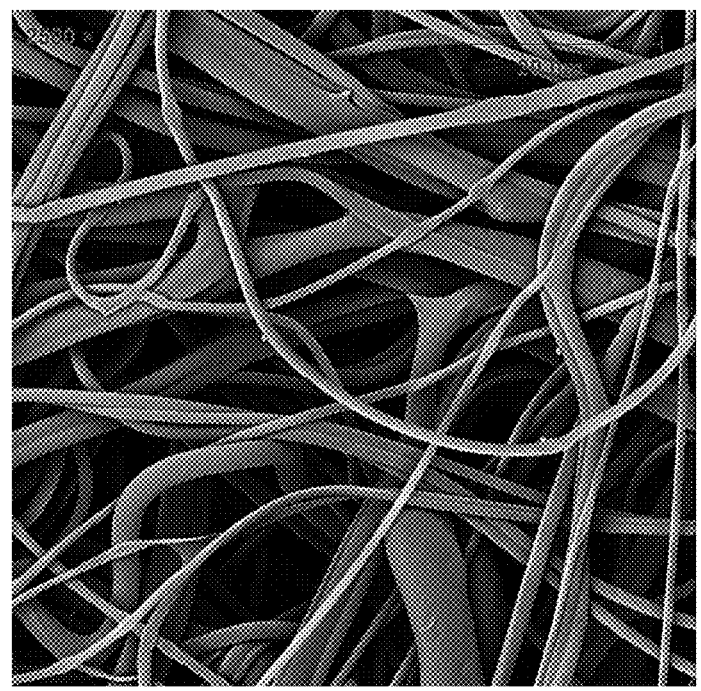

The calendered layer included a first nonwoven web and a second nonwoven web that were calendered together after formation. Before calendering, the first and second nonwoven webs each included meltblown polypropylene fibers having an average fiber diameter of 0.8 microns, had a basis weight of about 15 g/m², had a mean flow pore size of 9.1 microns, had a maximum pore size of about 20.7 microns, and an air permeability of about 48 CFM. The calendered layer had a basis weight of about 30 g/m², a mean flow pore size of 2.9 microns, a maximum pore size of about 7.3 microns, and an air permeability of about 4.4 CFM. The first and second coarse nonwoven webs were formed by a spunbond process and included polypropylene staple fibers having an average fiber diameter of 20 microns. The protective clothing material was formed by adhesively bonding the coarse fiber nonwoven webs to the calendered layer. Scanning electron microscope images of the calendered layer before (top) and after (bottom) calendering at an 1000× magnification and a 2500× magnification are shown in FIGS. 6A and 6B, respectively.

The properties of the protective clothing material, the comparative material of Comparative Example 1, and the existing material of Comparative Example 2 are shown in Table 1. Unless otherwise indicated, the structural and performance properties of the layers and entire protective clothing material were measured as described herein.

TABLE 1

Properties of the Protective Clothing Material, Comparative Material, and Conventional Material

| Property | Protective Clothing Material | Comparative Material | Existing Material |
|---|---|---|---|
| ASTM 1670 - 08(2014)e1 | Pass | Fail | Pass |
| ASTM 1671 - 13 (2013) | Pass | Fail | Pass |
| Basis weight | 62 g/m² | 62 g/m² | 72 g/m² |
| Air permeability | 4.4 CFM | 22 CFM | 0.11 CFM |
| Std. dev. in air permeability | 0.71 CFM | 2.2 CFM | — |
| Thickness | 12 mils | 18 mils | 12 mils |
| Mean flow pore size | 3 microns | 6.7 microns | 0.4 microns |
| Maximum pore size | 7 microns | 17.2 microns | 1.1 microns |

As shown in Table 1, the protective clothing material including a calendered layer passed ASTM 1670-08(2014) e1 and ASTM 1671-13 (2013) while having a relatively high air permeability and a relatively low basis weight and thickness.

Comparative Example 1

This example describes a comparative material including an uncalendered layer positioned between two coarse fiber nonwoven webs. The comparative material was formed as described in Example 1, except the first nonwoven web and the second nonwoven web were not calendered together after formation. The comparative material had a higher pore size, air permeability, and standard deviation in air permeability, but failed ASTM 1670-08(2014) e1 and ASTM 1671-13.

Comparative Example 2

This example describes an existing protective clothing material including film positioned between inner and outer fabric layers made of continuous fine filaments. The existing protective clothing material had a similar thickness, and protective rating as the protective clothing material in Example 1, but had a significantly lower air permeability and pore size.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A protective garment comprising:
    an electrospun fibrous layer comprising synthetic fibers;
    a first coarse fiber layer comprising fibers having an average fiber diameter of greater than or equal to about 10 microns; and
    a second coarse fiber layer comprising fibers having an average fiber diameter of greater than or equal to about 10 microns,
    wherein the electrospun fibrous layer is positioned between the coarse fiber layers.

2. The protective garment of claim 1, wherein a mean flow pore size of the electrospun fibrous layer is greater than or equal to about 1 micron and less than or equal to about 6 microns, a maximum pore size of the electrospun fibrous layer is greater than or equal to about 4 micron and less than or equal to about 12 microns and a difference between the maximum pore size and the mean pore size is less than or equal to about 6 microns, wherein the mean flow pore size and the maximum flow pore size are determined according to the standard ASTM F316-03 (2011).

3. The protective garment of claim 1, wherein an air permeability of the electrospun fibrous layer is greater than or equal to about 4 CFM and less than or equal to about 10 CFM.

4. The protective garment of claim 1, wherein the protective garment is configured as a surgical apparel or a surgical drape.

5. The protective garment of claim 1, wherein the average diameter of the synthetic fibers of the electrospun fibrous layer is greater than or equal to about 0.01 microns and less than or equal to about 0.05 microns.

6. The protective garment of claim 1, wherein the mean flow pore size of the electrospun fibrous layer is greater than or equal to about 2 microns and less than or equal to about 5 microns, wherein the mean flow pore size is determined according to the standard ASTM F316-03 (2011).

7. The protective garment of claim 1, wherein the maximum pore size of the electrospun fibrous layer is greater than or equal to about 6 microns and less than or equal to about 9 microns, wherein the maximum flow pore size is determined according to the standard ASTM F316-03 (2011).

8. The protective garment of claim 1, wherein the electrospun fibrous layer is less than or equal to about 6 mils.

9. The protective garment of claim 1, wherein the electrospun fibrous layer has a basis weight of less than or equal to about 50 g/m2.

10. The protective garment of claim 1, wherein the electrospun fibrous layer may have a moisture vapor transmission rate of greater than or equal to about 100 g/m2 day.

11. The protective garment of claim 1, wherein a standard deviation of an air permeability of the electrospun fibrous layer is greater than or equal to about 0 CFM and less than or equal to about 1 CFM.

* * * * *